(12) United States Patent
Finney et al.

(10) Patent No.: US 7,052,876 B1
(45) Date of Patent: May 30, 2006

(54) COMBINATORIAL METHOD FOR PRODUCING NUCLEIC ACIDS

(75) Inventors: Helene Margaret Finney, Maidenhead (GB); Alastair David Griffiths Lawson, Alresford (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/959,085

(22) PCT Filed: Apr. 17, 2000

(86) PCT No.: PCT/GB00/01498

§ 371 (c)(1),
(2), (4) Date: Oct. 16, 2001

(87) PCT Pub. No.: WO00/63360

PCT Pub. Date: Oct. 26, 2000

(30) Foreign Application Priority Data

Apr. 16, 1999 (GB) .............................. 9908814

(51) Int. Cl.
| | | |
|---|---|---|
| C12Q 1/68 | (2006.01) | |
| C12P 19/34 | (2006.01) | |
| C07H 21/02 | (2006.01) | |
| C07H 21/04 | (2006.01) | |
| C07H 19/00 | (2006.01) | |

(52) U.S. Cl. ..................... 435/91.1; 435/6; 435/7.1; 435/91.1; 435/91.2; 536/22.1; 536/23.1; 536/24.3; 536/24.31; 536/24.32; 536/24.33

(58) Field of Classification Search .............. 435/6, 435/7.1, 91.1, 91.2, 525; 536/22.1, 23.1, 536/24.3–24.33
See application file for complete search history.

(56) References Cited

U.S. PATENT DOCUMENTS 5,093,251 A    3/1992  Richards et al. .......... 435/172.3
5,863,730 A    1/1999  Masson et al. ................ 435/6

FOREIGN PATENT DOCUMENTS

| DE | 44 23 183 A1 | 7/1994 |
| DE | 196 33 427 A1 | 8/1996 |
| EP | 0 424 990 A1 | 5/1991 |
| WO | WO 90/00626 | 1/1990 |
| WO | WO 97/23613 | 7/1997 |
| WO | WO 98/17811 | 4/1998 |
| WO | WO 98/38326 | 9/1998 |
| WO | WO 99/00494 | 1/1999 |

OTHER PUBLICATIONS

Ioannon P. et al., "Two round enzymatic amplification combined with time–resolved fluorometry of Tb3+ chelates for enhanced sensitivity in DNA hybridization assays" *Analytical Chemistry*, 1998, 70, 698–702.

Sterky, F. et al., "Direct sequencing of bacterial artificial chromosomes (BACs) and prokaryotic genomes by biotin-capture PCR", *Journal of Biotechnology*, 1998, 60, 119–129.

*Biological Regulation and Development: Gene Expression* (ed. R.F. Goldberger).

Glover, *DNA cloning: a practical approach, vol. II: Expression systems*, IRL Press.

*Molecular Cloning: A Laboratory Manual* (Sambrook, et al.(1989).

Rees, A.R. et al., *Protein Engineering: A practical approach*, 1993, IRL Press.

*Primary Examiner*—Jeffrey Siew
(74) *Attorney, Agent, or Firm*—Woodcock Washburn LLP

(57) ABSTRACT

A method of generating novel nucleic acid molecules, by applying a combinatorial approach to the assembly of blocks of nucleic acid sequence, is described. By using restriction endonucleases having different recognition sites but which produce compatible cleavage products, a library of DNA molecules, of varying length and sequence, may be generated in a desired orientation.

40 Claims, 12 Drawing Sheets

FIG. 1

SEQUENTIAL SINGLE SEQUENCE ADDITION

Vector BamHI

```
ACG CGT G                              GA TCC TGA
TGC GCA CCT AG                            G ACT
 T   R                                         *

GA TCA ||||||||||||||G
  BclI               T ||||||||||||||CCT AG    BamHI

Annealed Oligos
```

Correct Orientation:

```
ACG CGT GGA TCA ||||||||||||||||GGA TCC TGA
TGC GCA CCT AGT ||||||||||||||||CCT AGG ACT
 T   R   G   S                   G   S   *
```

Wrong Orientation:

```
ACG CGT GGA TCA ||||||||||||||||TGA TCC TGA
TGC GCA CCT AGT ||||||||||||||||ACT AGG ACT
 T   R   G   S                   *   S   *
```

MULTIPLE ADDITION

```
BamH I                                  BamH I
    Bcl----Bam
                  Bcl----Bam
                              Bcl----Bam
```

CLONING CASSETTE FOR CONSTRUCTION OF CHIMERIC RECEPTORS WITH SYNTHETIC SIGNALLING COMPONENTS

FIG. 3
Range: 1 to 200

```
>SpeI
        10         20         30         40         50         60
         *          *          *          *          *          *
CG ACT AGT GAC AAA ACT CAC ACA TGC CCA CCG TGC CCA AAA CAC CTT TGT CCA AGT CCC
GC TGA TCA CTG TTT TGA GTG TGT ACG GGT GGC ACG GGT TTT CCC TTT GTG GAA ACA GGT TCA GGG
    S   D   K   T   H   T   C   P   P   C   P   K   G   K   F   L   C   P   S   P>
                                                                              A6083

>NarI
        70         80         90        100        110        120        130
         *          *          *          *          *          *          *
CTA TTT CCC GGA CCT TCT AAG CCC GGC GCC TTT TGG GTG CTG GAC GTG AGC CAC GAG GAC CTG GCT
GAT AAA GGG CCT GGA AGA TTC GGG CCG CGG AAA ACC CAC GAC CTG CAC TCG GTG CTC CTG GAC CGA
  L   F   P   G   P   S   K   P   G   A   F   W   V   L   D   V   S   H   E   D   L   A>
                      S0146                                                         >MluI
                                A6081

140        150        160        170        180        190
         *          *          *          *          *          *
TGC TAT AGC TTG CTA GTA ACA GTG GCC TTT ATT ATT TAA CGT GGA TCC TGA
ACG ATA TCG AAC GAT CAT TGT CAC CGG AAA TAA TAA ATT GCA CCT AGG ACT
  C   Y   S   L   L   V   T   V   A   F   I   I   *   R   G   S   *>
          A6082                                                     >BamHI

>EcoRI
               200
                 *
GAATTCATA    SEQ ID NO. 1
CTTAAGTAT    SEQ ID NO. 2
```

FIG. 4

OLIGONUCLEOTIDE SEQUENCES FOR CHIMERIC RECEPTOR CONSTRUCTION

All oligos are listed in the 5' to 3' orientation

S0146:CGACTAGTGACAAAACTCACACATGCCCACCGTGCCCAAAAGGGAAACACCT
TTGTCCAACTCCC (SEQ ID. NO. 22)

A6081:GCCTnTGGGTGCTGGTGGTGGTTGGTGGAGTCCTGGCTTGCTATAGCTTGC
TAGTAACAGTG (SEQ ID. NO. 23)

A6082:TATGAATTCTCAGGATCCACGCGTCACCCAGAAAATMTAAAGGCCACTGTTA
CTAGCAAGCTATAG (SEQ ID. NO. 24)

A6083:CACCACCAGCACCCAAAAGGCGCCGGGCTTAGAAGGTCCGGGAAATAGGGG
ACTTGGAC (SEQ ID. NO. 25)

A8810:GATCCTGGTTTCTCATGCTTCAGAGTCTCGTAAGTCTCCTGGTTCCTGGTGCT
CAGGCCCGTGTAACACCATCTGATTTCTCATAT (SEQ ID. NO. 26)

A8810B:GATCCTGGTTTCTCATGCTTCAGAGTATCGTAAGTCTCCTGGTTCCTGGTGC
TCAGGCCCGTGTAACACCATCTGATTTCTCATAT (SEQ ID. NO. 27)

A8811:GATCATATGAGAAATCAGATGGTGTTTACACGGGCCTGAGCACCAGGAACCA
GGAGACTTACGAGACTCTGAAGCATGAGAAACCAG (SEQ ID. NO. 28)

A8811 B:GATCATATGAGAAATCAGATGGTGTTTACACGGGCCTGAGCACCAGGAACC
AGGAGACTTACGATACTCTGAAGCATGAGAAACCAG (SEQ ID. NO. 29)

A8812:GATCCGGCCTGCATGTGAAGGGCGTCGTAGGTGTCCTTGGTGGCTGTACTGA
GACCCTGGTAMGGCCATCGTGCCCCTGTCCCCTT (SEQ ID. NO. 30)

A8813-.GATCAAGGGGCAAGGGGCACGATGGCCTTTACCAGGGTCTCAGTACAGCCA
CCAAGGACACCTACGACGCCCTTCACATGCAGGCCG (SEQ ID. NO. 31)

A8814:GATCCGCGCTCGCCTTTCATCCCAATCTCACTGTAGGCCTCCGCCATCTTATC
mCTGCAGTTCATTGTACAGGCCTTCCTGAGGGTTCTTCCTT (SEQ ID. NO. 32)

A8815:GATCAAGGAAGAACCCTCAGGMGGCCTGTACAATGAACTGCAGAAAGATAA
GATGGCGGAGGCCTACAGTGAGATTGGGATGAAAGGCGAGCGCG (SEQ ID. NO. 33)

A8816:GATCCCATCTCAGGGTCCCGGCCACGTCTCTTGTCCAAAACATCGTACTCCTC
TCTTCGTCCTAGATTGAGCTCGTTATAGAGCTGGTTCTGGCCT (SEQ ID. NO. 34)

A8817:GATCAGGCCAGAACCAGCTCTATAACGAGCTCAATCTAGGACGAAGAGGA
GTACGATGTTTTGGACAAGAGACGTGGCCGGGACCCTGAGATGG (SEQ ID. NO. 35)

A9000:GATCAGGAAACAAGGTTCCAGAGGATCGTGTTTATGAAGAATTAAACATATAT
TCAGCTACTTACAGTGAGTTGGAAGACCCAGGGGAAATGTCTCCTG (SEQ ID. NO. 36)

FIG. 4(contd.)

A9001:GATCCAGGAGACATTTCCCCTGGGTCTTCCAACTCACTGTAAGTAGCTGAATA
TATGTTTAATTCTTCATAAACACGATCCTCTGGAACCTTGTTTCCT (SEQ ID. NO. 37)

A9002:GATCAAAGCAGACTCTGTTGCCCAATGACCAGCTCTACCAGCCCCTCAAGGA
TCGAGAAGATGACCAGTACAGCCACCTTCAAGGAAACCAGTTGAGGG (SEQ ID. NO. 38)

A9003:GATCCCCTCAACTGGTTTCCTTGAAGGTGGCTGTACTGGTCATCTTCTCGATC
CTTGAGGGGCTGGTAGAGCTGGTCATTGGGCAACAGAGTCTGCTTT (SEQ ID. NO. 39)

A9004:GATCAGCTCTGTTGAGGAATGACCAGGTCTATCAGCCCCTCCGAGATCGAGA
TGATGCTCAGTACAGCCACCTTGGAGGAAACTGGGCTCGGAACAAGG (SEQ ID. NO. 40)

A9005:GATCCCTTGTTCCGAGCCCAGTTTCCTCCAAGGTGGCTGTACTGAGCATCATC
TCGATCTCGGAGGGGCTGATAGACCTGGTCATTCCTCAACAGAGCT (SEQ ID. NO. 41)

A9006:GATCACAAAACAAGGAGAGGCCACCACCTGTTCCCAACCCAGACTATGAGCC
CATCCGGAAAGGCCAGCGGGACCTGTATTCTGGCCTGAATCAGAGACGCATCG (SEQ ID. NO. 42)

A9007:GATCCGATGCGTCTCTGATTCAGGCCAGAATACAGGTCCCGCTGGCCTTTCC
GGATGGGCTCATAGTCTGGGTTGGGAACAGGTGGTGGCCTCTCCTTGTTTTGT (SEQ ID. NO. 43)

A9008:GATCACACGTGGATAACGAATACAGCCAACCTCCCAGGAACTCCCGCCTGTC
AGCTTATCCAGCTCTGGAAGGGGTTCTGCATCGCTCCG (SEQ ID. NO. 44)

A9009:GATCCGGAGCGATGCAGAACCCCTTCCAGAGCTGGATAAGCTGACAGGCGG
GAGTTCCTGGGAGGTTGGCTGTATTCGTTATCCACGTGT (SEQ ID. NO. 45)

A9010:GATCACCTCCCCGGACCTGCGATGACACGGTCACTTATTCAGCATTGCACAA
GCGCCAAGTGGGCGACTATGAGAACGTCATTCCAGATTTTCCAGAAGATGAGG (SEQ ID. NO. 46)

A9011:GATCCCTCATCTTCTGGAAAATCTGGAATGACGTTCTCATAGTCGCCCACTTG
GCGCTTGTGCAATGCTGAATAAGTGACCGTGTCATCGCAGGTCCGGGGAGGT (SEQ ID. NO. 47)

A9012:GATCAGAATATGAAGATGAAAACCT7TATGAAGGCCTGAACCTGGACGACTGC
TCCATGTATGAGGACATCTCCCGGGGCCTCCAGGGCACCTACCAGGATGTGG (SEQ ID. NO. 48)

A9013:GATCCCACATCCTGGTAGGTGCCCTGGAGGCCCCGGGAGATGTCCTCATACA
TGGAGCAGTCGTCCAGGTTCAGGCCTTCATAAAGGTTTTCATCTTCATATTCT (SEQ ID. NO. 49)

A9014:GATCAAAGGCTGGCATGGAGGAAGATCACACCTACGAGGGCCTGGACATTGA
CCAGACAGCCACCTATGAGGACATAGTGACGCTGCGGACAGGGGAAGTGG (SEQ ID. NO. 50)

A9015:GATCCCACTTCCCCTGTCCGCAGCGTCACTATGTCCTCATAGGTGGCTGTCT
GGTCAATGTCCAGGCCCTCGTAGGTGTGATCTTCCTCCATGCCAGCCTTT (SEQ ID. NO. 51)

FIG. 4(contd.)

A9016:GATCACCCCTACCCAACCCCAGGACAGCAGCTTCCATCTATGAGGAATTGCTA
AAACATGACACAAACATTTACTGCCGGATGGACCACAAAGCAGAAGTGGCTG (SEQ ID. NO. 52)

A9017:GATCCAGCCACTTCTGCTTTGTGGTCCATCCGGCAGTAAATGTTTGTGTCATG
TTTTAGCAATTCCTCATAGATGGAAGCTGCTGTCCTGGGGTTGGGTAGGGGT (SEQ ID. NO. 53)

A9018:GATCAAGGCTCCTGCACAGTGACTACATGAACATGACTCCTCGCCGACCAGG
GCCAACCCGCAAGCATTACCAGCCCTATGCCCCACCACGCGACTTCGCAG (SEQ ID. NO. 54)

A9019:GATCCTGCGAAGTCGCGTGGTGGGGCATAGGGCTGGTAATGCTTGCGGGTT
GGCCCTGGTCGGCGAGGAGTCATGTTCATGTAGTCACTGTGCAGGAGCCTT (SEQ ID. NO. 55)

A9020:GATCAATGATCGAAACATACAACCAAACTTCTCCCCGATCTGCGGCCACTGGA
CTGCCCATCAGCATGAAAG (SEQ ID. NO. 56)

A9021:GATCCTTTCATGCTGATGGGCAGTCCAGTGGCCGCAGATCGGGGAGAAGTTT
GGTTGTATGTTTCGATCATT (SEQ ID. NO. 57)

D7001:
GATCACAGAACCAGCTCTATVVSVNSNTAAATCTAGGACGAAGAGAGGAGTACWSV
NSNTAGACAAGAGACGTGGCCGGGACCCTGAGATGG (SEQ ID. NO. 58)

D7002:GATCCCATCTCAGGGTCCCGGCCACGTCTCTTGTCTANSNBSBBGTACTCCTCTCT
TC
GTCCTAGATTTANSNBSBBATAGAGCTGGTTCTGT (SEQ ID. NO. 59)

FIG. 5

THE AMINO ACID SEQUENCE OF SEQUENCE BLOCKS

The single letter amino acid code is used

| SEQ ID NO. | | |
|---|---|---|
| 3 | SB1 | GSGQNQLYNELNLGRREEYDVLDKRRGRDPEMGS |
| 5 | SB2 | GSRKNPQEGLYNELQKDKMAEAYSEIGMKGERGS |
| 6 | SB3 | GSRGKGHDGLYQGLSTATKDTYDALHMQAGS |
| 7 | SB4 | GSYEKSDGVYTGLSTRNQETYETLKHEKPGS |
| 8 | SB4* | GSYEKSDGVYTGLSTRNQETYDTLKHEKPGS |
| 10 | SB5 | GSGNKVPEDRVYEELNIYSATYSELEDPGEMSPGS |
| 11 | SB6 | GSKQTLLPNDQLYQPLKDREDDQYSHLQGNQLRGS |
| 12 | SB7 | GSALLRNDQVYQPLRDRDDAQYSHLGGNWARNKGS |
| 13 | SB8 | GSQNKERPPPVPNPDYEPIRKGQRDLYSGLNQRRIGS |
| 14 | SB9 | GSHVDNEYSQPPRNSRLSAYPALEGVLHRSGS |
| 15 | SB10 | GSPPRTCDDTVTYSALHKRQVGDYENVIPDFPEDEGS |
| 17 | SB11 | GSEYEDENLYEGLNLDDCSMYEDISRGLQGTYQDVGS |
| 18 | SB12 | GSKAGMEEDHTYEGLDIDQTATYEDIVTLRTGEVGS |
| 19 | SB13 | GSPLPNPRTAASIYEELLKHDTNIYCRMDHKAEVAGS |
| 20 | SB28 | GSRLLHSDYMNMTPRRPGPTRKHYQPYAPPRDFAGS |
| 21 | SB29 | GSMIETYNQTSPRSAATGLPISMKGS |

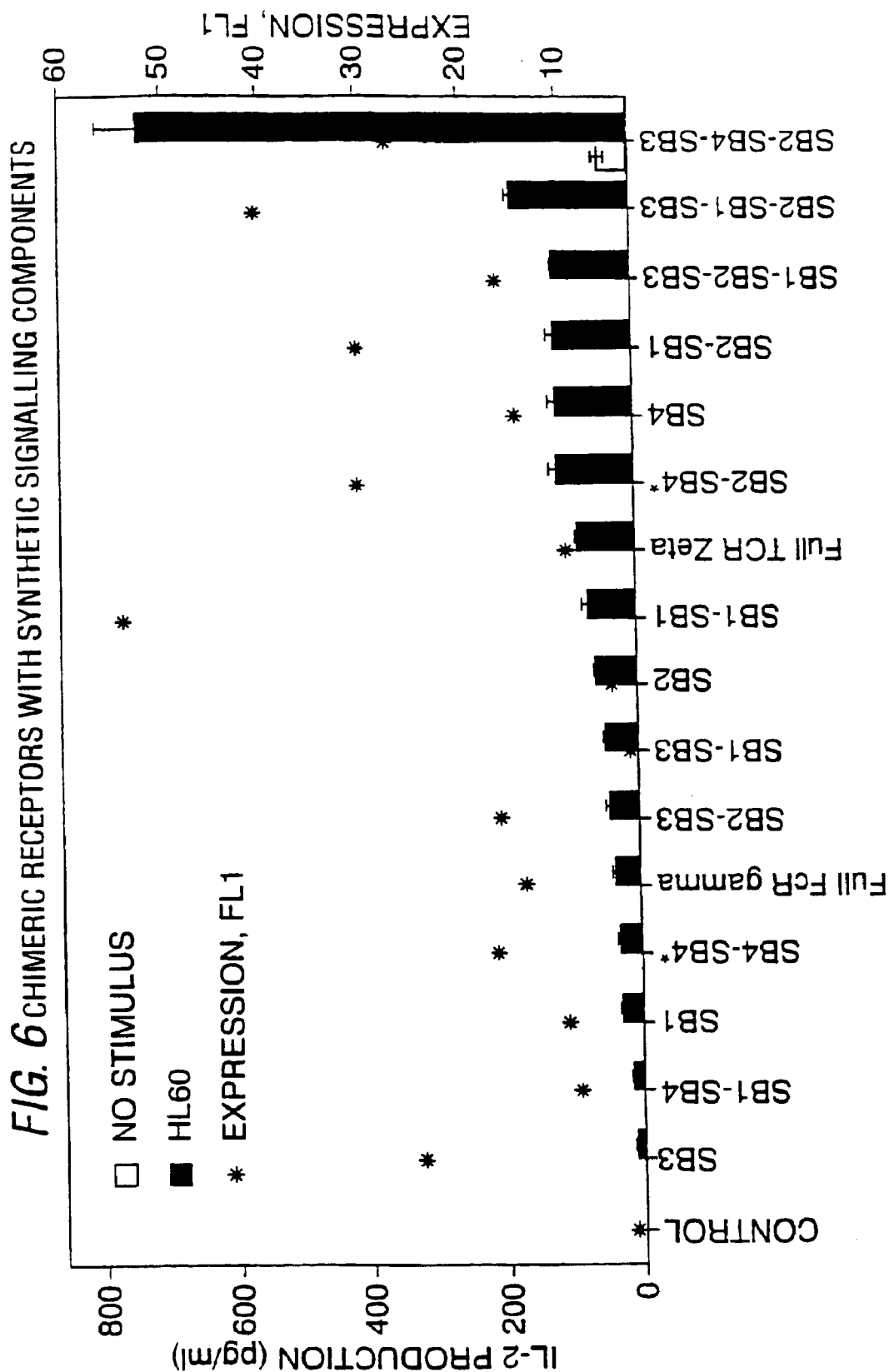
FIG. 6 CHIMERIC RECEPTORS WITH SYNTHETIC SIGNALLING COMPONENTS

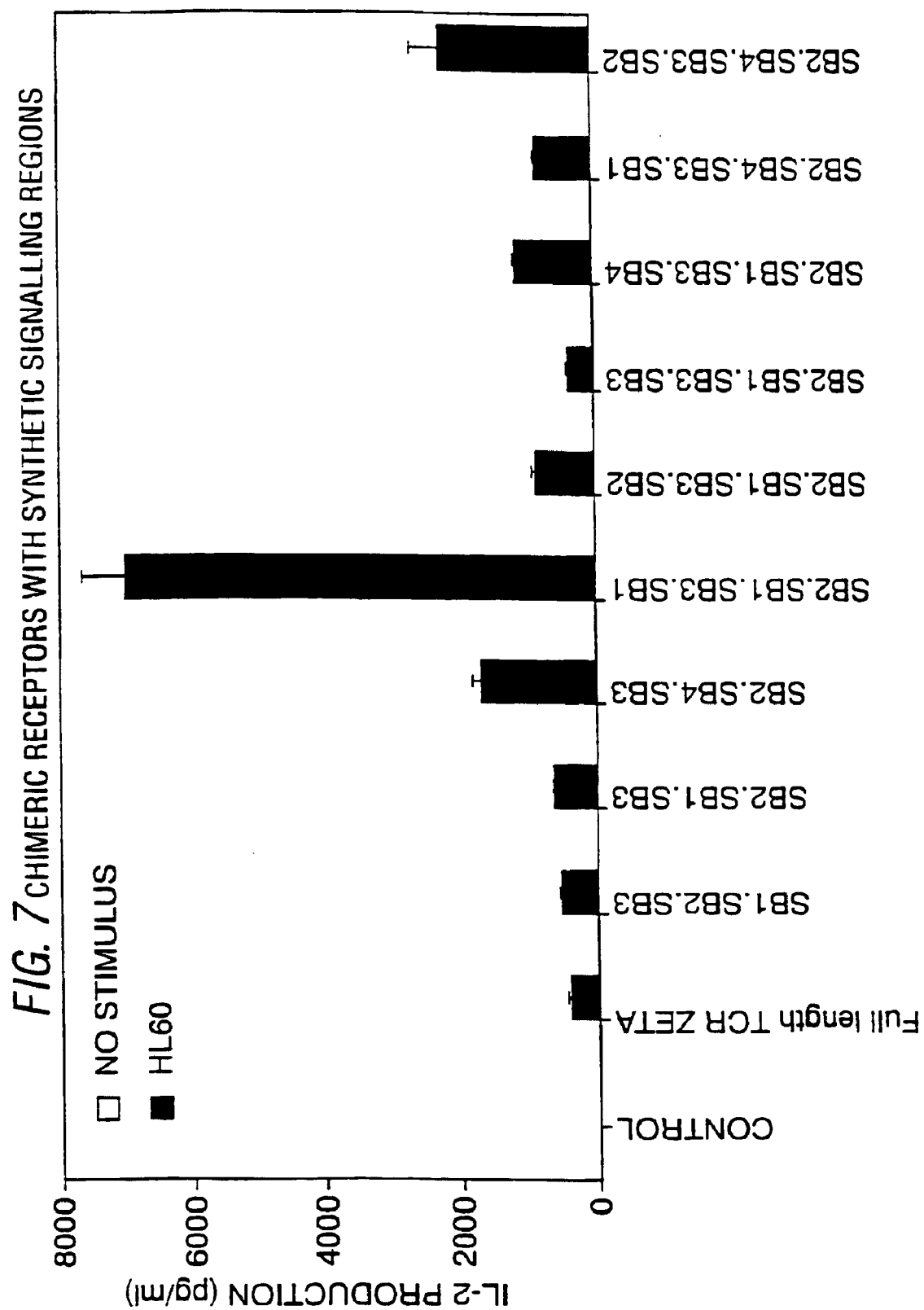
FIG. 7 CHIMERIC RECEPTORS WITH SYNTHETIC SIGNALLING REGIONS

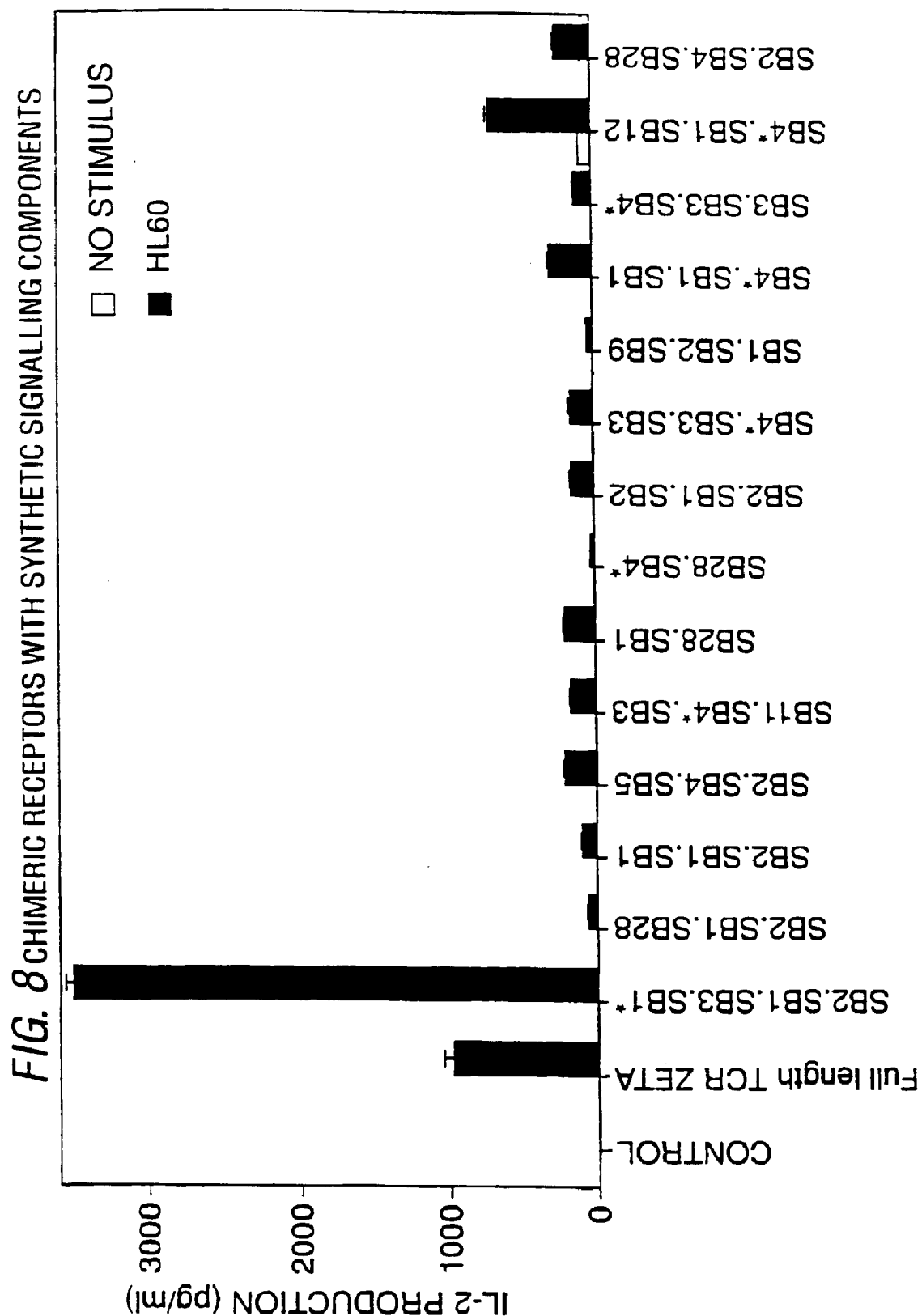

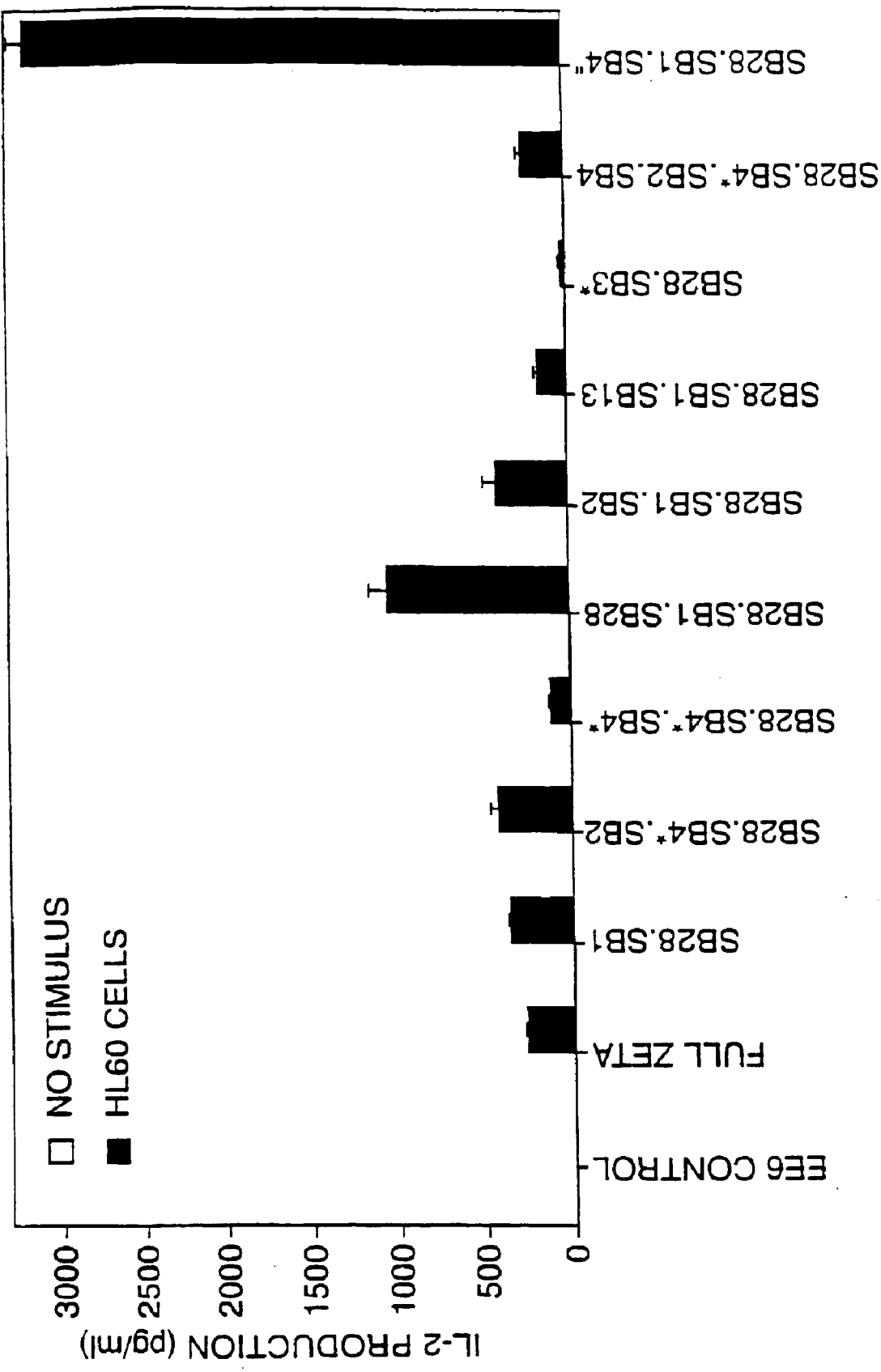

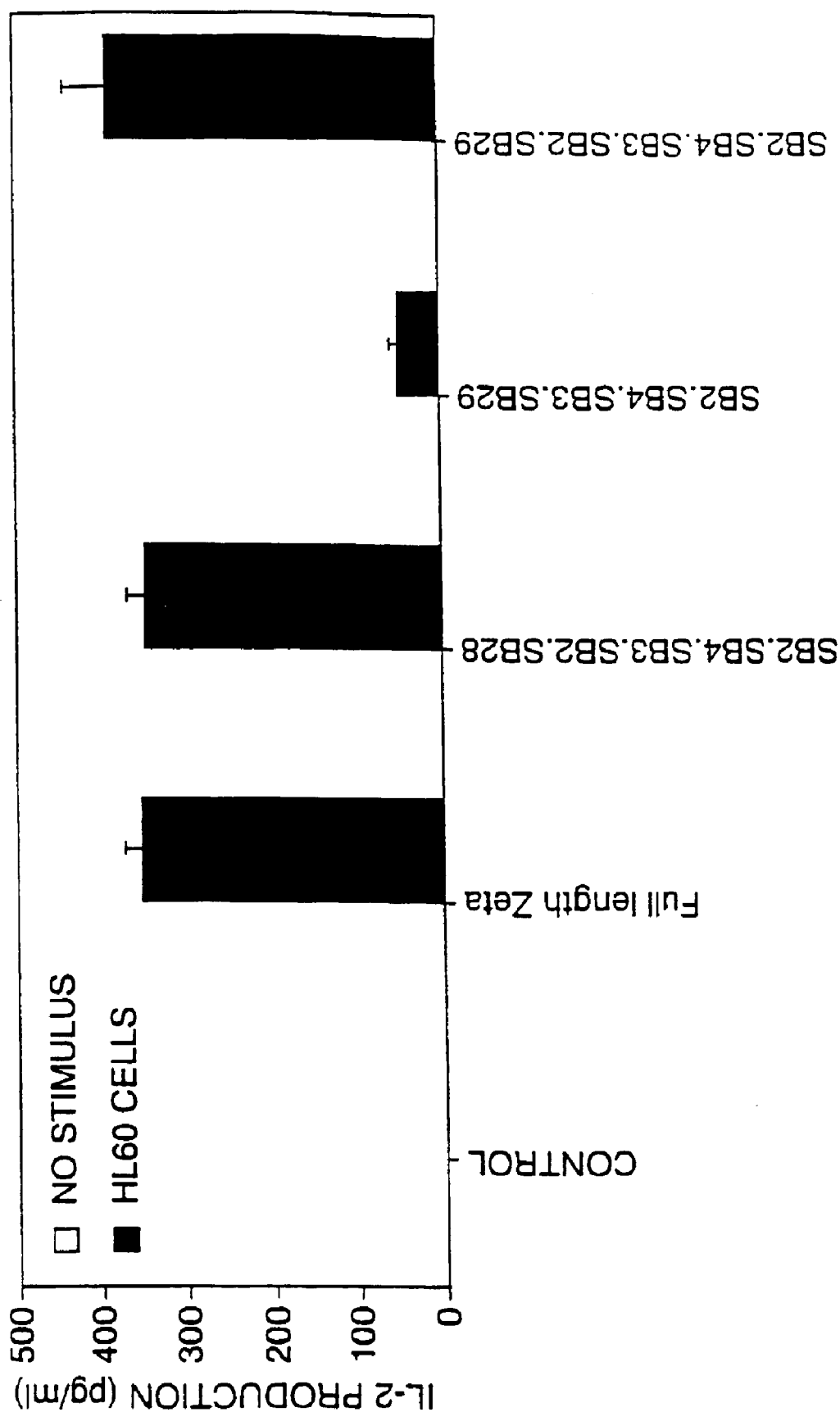

SEQUENCE LISTING

<160> NUMBER OF SEQ ID NOS: 63

<210> SEQ ID NO 1
<211> LENGTH: 200
<212> TYPE: DNA
<213> ORGANISM: Artificial Sequence
<220> FEATURE:
<223> OTHER INFORMATION: PCR Fragment (Figure 3 top)

<400> SEQUENCE: 1

```
cgactagtga caaaactcac acatgcccac cgtgcccaaa agggaaacac ctttgtccaa    60
gtcccctatt tcccggacct tctaagcccg gcgccttttg ggtgctggtg gtggttggtg   120
gagtcctggc ttgctatagc ttgctagtaa cagtggcctt tattattttc tgggtgacgc   180
gtggatcctg agaattcata                                              200
```

```
<210> SEQ ID NO 2
<211> LENGTH: 200
<212> TYPE: DNA
<213> ORGANISM: Artificial Sequence
<220> FEATURE:
<223> OTHER INFORMATION: PCR Fragment (Figure 3 bottom)

<400> SEQUENCE: 2
```

```
gctgatcact gttttgagtg tgtacgggtg gcacgggttt tcccttttgtg gaaacaggtt   60 caggggataa agggcctgga agattcgggc cgcggaaaac ccacgaccac caccaaccac  120
ctcaggaccg aacgatatcg aacgatcatt gtcaccggaa ataataaaag acccactgcg  180
cacctaggac tcttaagtat                                              200
```

```
<210> SEQ ID NO 3
<211> LENGTH: 34
<212> TYPE: PRT
<213> ORGANISM: Artificial Sequence
<220> FEATURE:
<223> OTHER INFORMATION: SB1

<400> SEQUENCE: 3
```

Gly Ser Gly Gln Asn Gln Leu Tyr Asn Glu Leu Asn Leu Gly Arg Arg
1               5                   10                  15

Glu Glu Tyr Asp Val Leu Asp Lys Arg Arg Gly Arg Asp Pro Glu Met
            20                  25                  30

Gly Ser

```
<210> SEQ ID NO 4
<211> LENGTH: 24
<212> TYPE: PRT
<213> ORGANISM: Artificial Sequence
<220> FEATURE:
<223> OTHER INFORMATION: SB1*

<400> SEQUENCE: 4
```

Gly Ser Gly Gln Asn Gln Leu Tyr Asn Glu Leu Asn Leu Gly Arg Arg
1               5                   10                  15

Glu Glu Tyr Asp Val Leu Ala Lys
            20

```
<210> SEQ ID NO 5
<211> LENGTH: 34
<212> TYPE: PRT
<213> ORGANISM: Artificial Sequence
<220> FEATURE:
<223> OTHER INFORMATION: SB2

<400> SEQUENCE: 5
```

Gly Ser Arg Lys Asn Pro Gln Glu Gly Leu Tyr Asn Glu Leu Gln Lys
1               5                   10                  15

Asp Lys Met Ala Glu Ala Tyr Ser Glu Ile Gly Met Lys Gly Glu Arg
            20                  25                  30

Gly Ser

```
<210> SEQ ID NO 6
<211> LENGTH: 31
<212> TYPE: PRT
<213> ORGANISM: Artificial Sequence
<220> FEATURE:
<223> OTHER INFORMATION: SB3

<400> SEQUENCE: 6

Gly Ser Arg Gly Lys Gly His Asp Gly Leu Tyr Gln Gly Leu Ser Thr
 1               5                  10                  15

Ala Thr Lys Asp Thr Tyr Asp Ala Leu His Met Gln Ala Gly Ser
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: SB4

<400> SEQUENCE: 7

Gly Ser Tyr Glu Lys Ser Asp Gly Val Tyr Thr Gly Leu Ser Thr Arg
 1               5                  10                  15

Asn Gln Glu Thr Tyr Glu Thr Leu Lys His Glu Lys Pro Gly Ser
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: SB4*

<400> SEQUENCE: 8

Gly Ser Tyr Glu Lys Ser Asp Gly Val Tyr Thr Gly Leu Ser Thr Arg
 1               5                  10                  15

Asn Gln Glu Thr Tyr Asp Thr Leu Lys His Glu Lys Pro Gly Ser
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: SB4"

<400> SEQUENCE: 9

Gly Leu Tyr Glu Lys Ser Asp Gly Val Tyr Thr Gly Leu Gly Thr Arg
 1               5                  10                  15

Asn Gln Glu Thr Tyr Glu Thr Leu Lys His Glu Lys Pro Gly Ser
            20                  25                  30

<210> SEQ ID NO 10
<211> LENGTH: 35
<212> TYPE: PRT
<213> ORGANISM: Artificial Sequence
<220> FEATURE:
<223> OTHER INFORMATION: SB5

<400> SEQUENCE: 10

Gly Ser Gly Asn Lys Val Pro Glu Asp Arg Val Tyr Glu Glu Leu Asn
 1               5                  10                  15

Ile Tyr Ser Ala Thr Tyr Ser Glu Leu Glu Asp Pro Gly Glu Met Ser
            20                  25                  30
```

-continued

Pro Gly Ser
        35

<210> SEQ ID NO 11
<211> LENGTH: 35
<212> TYPE: PRT
<213> ORGANISM: Artificial Sequence
<220> FEATURE:
<223> OTHER INFORMATION: SB6

<400> SEQUENCE: 11

Gly Ser Lys Gln Thr Leu Leu Pro Asn Asp Gln Leu Tyr Gln Pro Leu
1               5                   10                  15

Lys Asp Arg Glu Asp Asp Gln Tyr Ser His Leu Gln Gly Asn Gln Leu
            20                  25                  30

Arg Gly Ser
        35

<210> SEQ ID NO 12
<211> LENGTH: 35
<212> TYPE: PRT
<213> ORGANISM: Artificial Sequence
<220> FEATURE:
<223> OTHER INFORMATION: SB7

<400> SEQUENCE: 12

Gly Ser Ala Leu Leu Arg Asn Asp Gln Val Tyr Gln Pro Leu Arg Asp
1               5                   10                  15

Arg Asp Asp Ala Gln Tyr Ser His Leu Gly Gly Asn Trp Ala Arg Asn
            20                  25                  30

Lys Gly Ser
        35

<210> SEQ ID NO 13
<211> LENGTH: 37
<212> TYPE: PRT
<213> ORGANISM: Artificial Sequence
<220> FEATURE:
<223> OTHER INFORMATION: SB8

<400> SEQUENCE: 13

Gly Ser Gln Asn Lys Glu Arg Pro Pro Val Pro Asn Pro Asp Tyr
1               5                   10                  15

Glu Pro Ile Arg Lys Gly Gln Arg Asp Leu Tyr Ser Gly Leu Asn Gln
            20                  25                  30

Arg Arg Ile Gly Ser
        35

<210> SEQ ID NO 14
<211> LENGTH: 32
<212> TYPE: PRT
<213> ORGANISM: Artificial Sequence
<220> FEATURE:
<223> OTHER INFORMATION: SB9

<400> SEQUENCE: 14

Gly Ser His Val Asp Asn Glu Tyr Ser Gln Pro Pro Arg Asn Ser Arg
1               5                   10                  15

Leu Ser Ala Tyr Pro Ala Leu Glu Gly Val Leu His Arg Ser Gly Ser
            20                  25                  30

<210> SEQ ID NO 15
<211> LENGTH: 37

```
<212> TYPE: PRT
<213> ORGANISM: Artificial Sequence
<220> FEATURE:
<223> OTHER INFORMATION: SB10

<400> SEQUENCE: 15

Gly Ser Pro Pro Arg Thr Cys Asp Asp Thr Val Thr Tyr Ser Ala Leu
1               5                   10                  15

His Lys Arg Gln Val Gly Asp Tyr Glu Asn Val Ile Pro Asp Phe Pro
            20                  25                  30

Glu Asp Glu Gly Ser
        35

<210> SEQ ID NO 16
<211> LENGTH: 31
<212> TYPE: PRT
<213> ORGANISM: Artificial Sequence
<220> FEATURE:
<223> OTHER INFORMATION: SB10*

<400> SEQUENCE: 16

Gly Ser Pro Pro Arg Thr Cys Asp Asp Thr Val Thr Tyr Ser Ala Leu
1               5                   10                  15

His Lys Arg Gln Val Gly Asp Tyr Glu Asn Val Ile Pro Glu Arg
            20                  25                  30

<210> SEQ ID NO 17
<211> LENGTH: 37
<212> TYPE: PRT
<213> ORGANISM: Artificial Sequence
<220> FEATURE:
<223> OTHER INFORMATION: SB11

<400> SEQUENCE: 17

Gly Ser Glu Tyr Glu Asp Glu Asn Leu Tyr Glu Gly Leu Asn Leu Asp
1               5                   10                  15

Asp Cys Ser Met Tyr Glu Asp Ile Ser Arg Gly Leu Gln Gly Thr Tyr
            20                  25                  30

Gln Asp Val Gly Ser
        35

<210> SEQ ID NO 18
<211> LENGTH: 36
<212> TYPE: PRT
<213> ORGANISM: Artificial Sequence
<220> FEATURE:
<223> OTHER INFORMATION: SB12

<400> SEQUENCE: 18

Gly Ser Lys Ala Gly Met Glu Glu Asp His Thr Tyr Glu Gly Leu Asp
1               5                   10                  15

Ile Asp Gln Thr Ala Thr Tyr Asp Ile Val Thr Leu Arg Thr Gly
            20                  25                  30

Glu Val Gly Ser
        35

<210> SEQ ID NO 19
<211> LENGTH: 37
<212> TYPE: PRT
<213> ORGANISM: Artificial Sequence
<220> FEATURE:
<223> OTHER INFORMATION: SB13

<400> SEQUENCE: 19
```

-continued

Gly Ser Pro Leu Pro Asn Pro Arg Thr Ala Ala Ser Ile Tyr Glu Glu
1               5                   10                  15

Leu Leu Lys His Asp Thr Asn Ile Tyr Cys Arg Met Asp His Lys Ala
                20                  25                  30

Glu Val Ala Gly Ser
            35

<210> SEQ ID NO 20
<211> LENGTH: 36
<212> TYPE: PRT
<213> ORGANISM: Artificial Sequence
<220> FEATURE:
<223> OTHER INFORMATION: SB28

<400> SEQUENCE: 20

Gly Ser Arg Leu Leu His Ser Asp Tyr Met Asn Met Thr Pro Arg Arg
1               5                   10                  15

Pro Gly Pro Thr Arg Lys His Tyr Gln Pro Tyr Ala Pro Pro Arg Asp
                20                  25                  30

Phe Ala Gly Ser
        35

<210> SEQ ID NO 21
<211> LENGTH: 26
<212> TYPE: PRT
<213> ORGANISM: Artificial Sequence
<220> FEATURE:
<223> OTHER INFORMATION: SB29

<400> SEQUENCE: 21

Gly Ser Met Ile Glu Thr Tyr Asn Gln Thr Ser Pro Arg Ser Ala Ala
1               5                   10                  15

Thr Gly Leu Pro Ile Ser Met Lys Gly Ser
            20                  25

<210> SEQ ID NO 22
<211> LENGTH: 65
<212> TYPE: DNA
<213> ORGANISM: Artificial Sequence
<220> FEATURE:
<223> OTHER INFORMATION: S0146

<400> SEQUENCE: 22
cgactagtga caaaactcac acatgcccac cgtgcccaaa agggaaacac ctttgtccaa      60
ctccc                                                                 65

<210> SEQ ID NO 23
<211> LENGTH: 63
<212> TYPE: DNA
<213> ORGANISM: Artificial Sequence
<220> FEATURE:
<223> OTHER INFORMATION: A6081

<400> SEQUENCE: 23
gcctttnggg tgctggtggt ggttggtgga gtcctggctt gctatagctt gctagtaaca      60
gtg                                                                   63

<210> SEQ ID NO 24
<211> LENGTH: 67
<212> TYPE: DNA
<213> ORGANISM: Artificial Sequence
<220> FEATURE:

```
<223> OTHER INFORMATION: A6082

<400> SEQUENCE: 24
tatgaattct caggatccac gcgtcaccca gaaaataata aaggccactg ttactagcaa      60
gctatag                                                                67

<210> SEQ ID NO 25
<211> LENGTH: 59
<212> TYPE: DNA
<213> ORGANISM: Artificial Sequence
<220> FEATURE:
<223> OTHER INFORMATION: A6083

<400> SEQUENCE: 25
caccaccagc acccaaaagg cgccgggctt agaaggtccg ggaaataggg gacttggac       59

<210> SEQ ID NO 26
<211> LENGTH: 86
<212> TYPE: DNA
<213> ORGANISM: Artificial Sequence
<220> FEATURE:
<223> OTHER INFORMATION: A8810

<400> SEQUENCE: 26
gatcctggtt tctcatgctt cagagtctcg taagtctcct ggttcctggt gctcaggccc      60
gtgtaacacc atctgatttc tcatat                                           86

<210> SEQ ID NO 27
<211> LENGTH: 86
<212> TYPE: DNA
<213> ORGANISM: Artificial Sequence
<220> FEATURE:
<223> OTHER INFORMATION: A8810B

<400> SEQUENCE: 27
gatcctggtt tctcatgctt cagagtatcg taagtctcct ggttcctggt gctcaggccc      60
gtgtaacacc atctgatttc tcatat                                           86

<210> SEQ ID NO 28
<211> LENGTH: 87
<212> TYPE: DNA
<213> ORGANISM: Artificial Sequence
<220> FEATURE:
<223> OTHER INFORMATION: A8811

<400> SEQUENCE: 28
gatcatatga gaaatcagat ggtgtttaca cgggcctgag caccaggaac caggagactt      60
acgagactct gaagcatgag aaaccag                                          87

<210> SEQ ID NO 29
<211> LENGTH: 87
<212> TYPE: DNA
<213> ORGANISM: Artificial Sequence
<220> FEATURE:
<223> OTHER INFORMATION: A8811B

<400> SEQUENCE: 29
gatcatatga gaaatcagat ggtgtttaca cgggcctgag caccaggaac caggagactt      60
acgatactct gaagcatgag aaaccag                                          87

<210> SEQ ID NO 30
<211> LENGTH: 87
```

```
<212> TYPE: DNA
<213> ORGANISM: Artificial Sequence
<220> FEATURE:
<223> OTHER INFORMATION: A8812

<400> SEQUENCE: 30
gatccggcct gcatgtgaag ggcgtcgtag gtgtccttgg tggctgtact gagaccctgg    60
taaaggccat cgtgcccctg tcccctt                                        87

<210> SEQ ID NO 31
<211> LENGTH: 87
<212> TYPE: DNA
<213> ORGANISM: Artificial Sequence
<220> FEATURE:
<223> OTHER INFORMATION: A8813

<400> SEQUENCE: 31
gatcaagggg caaggggcac gatggccttt accagggtct cagtacagcc accaaggaca    60
cctacgacgc ccttcacatg caggccg                                        87

<210> SEQ ID NO 32
<211> LENGTH: 96
<212> TYPE: DNA
<213> ORGANISM: Artificial Sequence
<220> FEATURE:
<223> OTHER INFORMATION: A8814

<400> SEQUENCE: 32
gatccgcgct cgcctttcat cccaatctca ctgtaggcct ccgccatctt atctttctgc    60
agttcattgt acaggccttc ctgagggttc ttcctt                              96

<210> SEQ ID NO 33
<211> LENGTH: 96
<212> TYPE: DNA
<213> ORGANISM: Artificial Sequence
<220> FEATURE:
<223> OTHER INFORMATION: A8815

<400> SEQUENCE: 33
gatcaaggaa gaaccctcag gaaggcctgt acaatgaact gcagaaagat aagatggcgg    60
aggcctacag tgagattggg atgaaaggcg agcgcg                              96

<210> SEQ ID NO 34
<211> LENGTH: 96
<212> TYPE: DNA
<213> ORGANISM: Artificial Sequence
<220> FEATURE:
<223> OTHER INFORMATION: A8816

<400> SEQUENCE: 34
gatcccatct cagggtcccg gccacgtctc ttgtccaaaa catcgtactc ctctcttcgt    60
cctagattga gctcgttata gagctggttc tggcct                              96

<210> SEQ ID NO 35
<211> LENGTH: 96
<212> TYPE: DNA
<213> ORGANISM: Artificial Sequence
<220> FEATURE:
<223> OTHER INFORMATION: A8817

<400> SEQUENCE: 35
gatcaggcca gaaccagctc tataacgagc tcaatctagg acgaagagag gagtacgatg    60
```
ttttggacaa gagacgtggc cgggaccctg agatgg        96

<210> SEQ ID NO 36
<211> LENGTH: 99
<212> TYPE: DNA
<213> ORGANISM: Artificial Sequence
<220> FEATURE:
<223> OTHER INFORMATION: A9000

<400> SEQUENCE: 36
gatcaggaaa caaggttcca gaggatcgtg tttatgaaga attaaacata tattcagcta    60
cttacagtga gttggaagac ccaggggaaa tgtctcctg                           99

<210> SEQ ID NO 37
<211> LENGTH: 99
<212> TYPE: DNA
<213> ORGANISM: Artificial Sequence
<220> FEATURE:
<223> OTHER INFORMATION: A9001

<400> SEQUENCE: 37
gatccaggag acatttcccc tgggtcttcc aactcactgt aagtagctga atatatgttt    60
aattcttcat aaacacgatc ctctggaacc ttgtttcct                           99

<210> SEQ ID NO 38
<211> LENGTH: 99
<212> TYPE: DNA
<213> ORGANISM: Artificial Sequence
<220> FEATURE:
<223> OTHER INFORMATION: A9002

<400> SEQUENCE: 38
gatcaaagca gactctgttg cccaatgacc agctctacca gcccctcaag gatcgagaag    60
atgaccagta cagccacctt caaggaaacc agttgaggg                           99

<210> SEQ ID NO 39
<211> LENGTH: 99
<212> TYPE: DNA
<213> ORGANISM: Artificial Sequence
<220> FEATURE:
<223> OTHER INFORMATION: A9003

<400> SEQUENCE: 39
gatcccctca actggtttcc ttgaaggtgg ctgtactggt catcttctcg atccttgagg    60
ggctggtaga gctggtcatt gggcaacaga gtctgctttt                          99

<210> SEQ ID NO 40
<211> LENGTH: 99
<212> TYPE: DNA
<213> ORGANISM: Artificial Sequence
<220> FEATURE:
<223> OTHER INFORMATION: A9004

<400> SEQUENCE: 40
gatcagctct gttgaggaat gaccaggtct atcagcccct ccgagatcga gatgatgctc    60
agtacagcca ccttggagga aactgggctc ggaacaagg                           99

<210> SEQ ID NO 41
<211> LENGTH: 99
<212> TYPE: DNA
<213> ORGANISM: Artificial Sequence
<220> FEATURE:
<223> OTHER INFORMATION: A9005

<400> SEQUENCE: 41
gatcccttgt tccgagccca gtttcctcca aggtggctgt actgagcatc atctcgatct    60 cggagggct atagacctg gtcattcctc aacagagct    99

<210> SEQ ID NO 42
<211> LENGTH: 105
<212> TYPE: DNA
<213> ORGANISM: Artificial Sequence
<220> FEATURE:
<223> OTHER INFORMATION: A9006

<400> SEQUENCE: 42
gatcacaaaa caaggagagg ccaccacctg ttcccaaccc agactatgag cccatccgga    60
aaggccagcg ggacctgtat tctggcctga atcagagacg catcg    105

<210> SEQ ID NO 43
<211> LENGTH: 105
<212> TYPE: DNA
<213> ORGANISM: Artificial Sequence
<220> FEATURE:
<223> OTHER INFORMATION: A9007

<400> SEQUENCE: 43
gatccgatgc gtctctgatt caggccagaa tacaggtccc gctggccttt ccggatgggc    60
tcatagtctg ggttgggaac aggtggtggc ctctccttgt tttgt    105

<210> SEQ ID NO 44
<211> LENGTH: 90
<212> TYPE: DNA
<213> ORGANISM: Artificial Sequence
<220> FEATURE:
<223> OTHER INFORMATION: A9008

<400> SEQUENCE: 44
gatcacacgt ggataacgaa tacagccaac ctcccaggaa ctcccgcctg tcagcttatc    60
cagctctgga aggggttctg catcgctccg    90

<210> SEQ ID NO 45
<211> LENGTH: 90
<212> TYPE: DNA
<213> ORGANISM: Artificial Sequence
<220> FEATURE:
<223> OTHER INFORMATION: A9009

<400> SEQUENCE: 45
gatccggagc gatgcagaac cccttccaga gctggataag ctgacaggcg ggagttcctg    60
ggaggttggc tgtattcgtt atccacgtgt    90

<210> SEQ ID NO 46
<211> LENGTH: 105
<212> TYPE: DNA
<213> ORGANISM: Artificial Sequence
<220> FEATURE:
<223> OTHER INFORMATION: A9010

<400> SEQUENCE: 46
gatcacctcc ccggacctgc gatgacacgg tcacttattc agcattgcac aagcgccaag    60
tgggcgacta tgagaacgtc attccagatt ttccagaaga tgagg    105

<210> SEQ ID NO 47

```
<211> LENGTH: 105
<212> TYPE: DNA
<213> ORGANISM: Artificial Sequence
<220> FEATURE:
<223> OTHER INFORMATION: A9011

<400> SEQUENCE: 47
gatccctcat cttctggaaa atctggaatg acgttctcat agtcgcccac ttggcgcttg      60
tgcaatgctg aataagtgac cgtgtcatcg caggtccggg gaggt                    105

<210> SEQ ID NO 48
<211> LENGTH: 105
<212> TYPE: DNA
<213> ORGANISM: Artificial Sequence
<220> FEATURE:
<223> OTHER INFORMATION: A9012

<400> SEQUENCE: 48
gatcagaata tgaagatgaa aacctttatg aaggcctgaa cctggacgac tgctccatgt      60
atgaggacat ctcccggggc ctccagggca cctaccagga tgtgg                    105

<210> SEQ ID NO 49
<211> LENGTH: 105
<212> TYPE: DNA
<213> ORGANISM: Artificial Sequence
<220> FEATURE:
<223> OTHER INFORMATION: A9013

<400> SEQUENCE: 49
gatcccacat cctggtaggt gccctggagg ccccgggaga tgtcctcata catggagcag      60
tcgtccaggt tcaggccttc ataaaggttt tcatcttcat attct                    105

<210> SEQ ID NO 50
<211> LENGTH: 102
<212> TYPE: DNA
<213> ORGANISM: Artificial Sequence
<220> FEATURE:
<223> OTHER INFORMATION: A9014

<400> SEQUENCE: 50
gatcaaaggc tggcatggag gaagatcaca cctacgaggg cctggacatt gaccagacag      60
ccacctatga ggacatagtg acgctgcgga caggggaagt gg                       102

<210> SEQ ID NO 51
<211> LENGTH: 102
<212> TYPE: DNA
<213> ORGANISM: Artificial Sequence
<220> FEATURE:
<223> OTHER INFORMATION: A9015

<400> SEQUENCE: 51
gatcccactt ccctgtccg cagcgtcact atgtcctcat aggtggctgt ctggtcaatg       60
tccaggccct cgtaggtgtg atcttcctcc atgccagcct tt                       102

<210> SEQ ID NO 52
<211> LENGTH: 105
<212> TYPE: DNA
<213> ORGANISM: Artificial Sequence
<220> FEATURE:
<223> OTHER INFORMATION: A9016

<400> SEQUENCE: 52
gatcacccct acccaacccc aggacagcag cttccatcta tgaggaattg ctaaaacatg      60
```
acacaaacat tactgccgg atggaccaca aagcagaagt ggctg 105

<210> SEQ ID NO 53
<211> LENGTH: 105
<212> TYPE: DNA
<213> ORGANISM: Artificial Sequence
<220> FEATURE:
<223> OTHER INFORMATION: A9017

<400> SEQUENCE: 53
gatccagcca cttctgcttt gtggtccatc cggcagtaaa tgtttgtgtc atgttttagc 60
aattcctcat agatggaagc tgctgtcctg gggttgggta ggggt 105

<210> SEQ ID NO 54
<211> LENGTH: 102
<212> TYPE: DNA
<213> ORGANISM: Artificial Sequence
<220> FEATURE:
<223> OTHER INFORMATION: A9018

<400> SEQUENCE: 54
gatcaaggct cctgcacagt gactacatga acatgactcc tcgccgacca gggccaaccc 60
gcaagcatta ccagccctat gccccaccac gcgacttcgc ag 102

<210> SEQ ID NO 55
<211> LENGTH: 102
<212> TYPE: DNA
<213> ORGANISM: Artificial Sequence
<220> FEATURE:
<223> OTHER INFORMATION: A9019

<400> SEQUENCE: 55
gatcctgcga agtcgcgtgg tgggcatag ggctggtaat gcttgcgggt tggccctggt 60
cggcgaggag tcatgttcat gtagtcactg tgcaggagcc tt 102

<210> SEQ ID NO 56
<211> LENGTH: 72
<212> TYPE: DNA
<213> ORGANISM: Artificial Sequence
<220> FEATURE:
<223> OTHER INFORMATION: A9020

<400> SEQUENCE: 56
gatcaatgat cgaaacatac aaccaaactt ctccccgatc tgcggccact ggactgccca 60
tcagcatgaa ag 72

<210> SEQ ID NO 57
<211> LENGTH: 72
<212> TYPE: DNA
<213> ORGANISM: Artificial Sequence
<220> FEATURE:
<223> OTHER INFORMATION: A9021

<400> SEQUENCE: 57
gatcctttca tgctgatggg cagtccagtg gccgcagatc ggggagaagt ttggttgtat 60
gtttcgatca tt 72

<210> SEQ ID NO 58
<211> LENGTH: 93
<212> TYPE: DNA
<213> ORGANISM: Artificial Sequence
<220> FEATURE:

-continued

<223> OTHER INFORMATION: D7001
<221> NAME/KEY: misc_feature
<222> LOCATION: (25)..(25)
<223> OTHER INFORMATION: N is any nucleotide
<221> NAME/KEY: misc_feature
<222> LOCATION: (27)..(27)
<223> OTHER INFORMATION: N is any nucleotide
<221> NAME/KEY: misc_feature
<222> LOCATION: (58)..(58)
<223> OTHER INFORMATION: N is any nucleotide
<221> NAME/KEY: misc_feature
<222> LOCATION: (60)..(60)
<223> OTHER INFORMATION: N is any nucleotide

<400> SEQUENCE: 58
gatcacagaa ccagctctat vvsvnsntaa atctaggacg aagagaggag tacvvsvnsn     60
tagacaagag acgtggccgg gaccctgaga tgg                                 93

<210> SEQ ID NO 59
<211> LENGTH: 93
<212> TYPE: DNA
<213> ORGANISM: Artificial Sequence
<220> FEATURE:
<223> OTHER INFORMATION: D7002
<221> NAME/KEY: misc_feature
<222> LOCATION: (38)..(38)
<223> OTHER INFORMATION: N is any nucleotide
<221> NAME/KEY: misc_feature
<222> LOCATION: (40)..(40)
<223> OTHER INFORMATION: N is any nucleotide
<221> NAME/KEY: misc_feature
<222> LOCATION: (71)..(71)
<223> OTHER INFORMATION: N is any nucleotide
<221> NAME/KEY: misc_feature
<222> LOCATION: (73)..(73)
<223> OTHER INFORMATION: N is any nucleotide

<400> SEQUENCE: 59
gatcccatct cagggtcccg gccacgtctc ttgtctansn bsbbgtactc ctctcttcgt     60
cctagattta nsnbsbbata gagctggttc tgt                                 93

<210> SEQ ID NO 60
<211> LENGTH: 33
<212> TYPE: PRT
<213> ORGANISM: Artificial Sequence
<220> FEATURE:
<223> OTHER INFORMATION: SBW1A

<400> SEQUENCE: 60

Gly Ser Gln Asn Gln Leu Tyr Pro Pro Leu Asn Leu Gly Arg Arg Glu
1               5                   10                  15

Glu Tyr Arg Pro Leu Asp Lys Arg Arg Gly Arg Asp Pro Glu Met Gly
            20                  25                  30

Ser

<210> SEQ ID NO 61
<211> LENGTH: 33
<212> TYPE: PRT
<213> ORGANISM: Artificial Sequence
<220> FEATURE:
<223> OTHER INFORMATION: SBW1B

<400> SEQUENCE: 61

Gly Ser Gln Asn Gln Leu Tyr Gly Gly Leu Asn Leu Gly Arg Arg Glu
1               5                   10                  15

Glu Tyr Gly Lys Ile Asp Lys Arg Arg Gly Arg Asp Pro Glu Met Gly
            20                  25                  30

```
Ser

<210> SEQ ID NO 62
<211> LENGTH: 33
<212> TYPE: PRT
<213> ORGANISM: Artificial Sequence
<220> FEATURE:
<223> OTHER INFORMATION: SBW1C

<400> SEQUENCE: 62

Gly Ser Gln Asn Gln Leu Tyr Gly Ala Val Asn Leu Gly Arg Arg Glu
1               5                   10                  15

Glu Tyr Thr Gly Val Asp Lys Arg Arg Gly Arg Asp Pro Glu Met Gly
            20                  25                  30

Ser

<210> SEQ ID NO 63
<211> LENGTH: 33
<212> TYPE: PRT
<213> ORGANISM: Artificial Sequence
<220> FEATURE:
<223> OTHER INFORMATION: SBW1D

<400> SEQUENCE: 63

Gly Ser Gln Asn Gln Leu Tyr Thr Gly Ile Asn Leu Gly Arg Arg Glu
1               5                   10                  15

Glu Tyr Gly Thr Val Asp Lys Arg Arg Gly Arg Asp Pro Glu Met Gly
            20                  25                  30

Ser
```

COMBINATORIAL METHOD FOR PRODUCING NUCLEIC ACIDS

The present invention relates to a method for the generation of novel nucleic acid molecules and proteins, and to nucleic acids and proteins produced by such a method. The invention allows the generation in vitro of new biological products formed by applying a combinatorial approach to blocks of nucleic acid sequence.

Advances in recombinant DNA technology over the last decade or so have meant that it has become possible to construct synthetic genes and, consequently, synthetic proteins. Molecules may now be rationally designed and produced with the aim of improving their efficacy over that of a sequence that occurs naturally.

Various techniques now exist for the generation of libraries of proteins, most using methods that allow the random combination of a number of peptides to produce a library of variants. Molecules having the desired characteristics can be isolated through selection regimes that select for a desired phenotype, such as a particular biochemical or biological activity.

Phage display provides one example of a technology that has been highly successful in allowing for the selection of a displayed protein (for reviews see Clackson and Wells, 1994, Hoogenboom HR, 1997 and Lowman HB, 1997). Additionally, combinatorial chemistry can be used to generate peptides of random sequence (Lom KS, 1997).

Existing methods for the generation of libraries of peptides or proteins are limited by pre-design requirements, the number of molecules in the library and the small size of the products obtained. The present invention advantageously provides a method that facilitates the generation of new genes and proteins of unlimited size, assembled in either a predetermined and/or random order, and also allows their subsequent analysis. This method utilises compatible restriction enzymes and ligation to build DNA molecules from smaller, naturally occurring and/or synthetic DNA in a desired orientation.

Thus according to one aspect of the present invention there is provided a method of generating a library of DNA molecules of varying length and sequence in a desired orientation comprising the steps of:
a) providing a mixture of double-stranded DNA molecules, each of said molecules having 5' and 3' ends which are compatible to each other and correspond to the cleavage products of different but compatible restriction enzymes; and
b) allowing ligation to take place, wherein ligation of said double-stranded DNA molecules in desired orientations generates molecules that are not cut by either of said restriction enzymes whereas ligation in undesired orientations generates molecules that retain at one or more ligation points a restriction site that is recognised by one of said restriction enzymes; and
c) cutting the ligated DNA molecules with one or both of said restriction enzymes such that only molecules that are ligated in undesired orientations are cut, leaving a library DNA molecules of varying length and sequence in a desired orientation.

Where desired the mixture of double-stranded DNA molecules in step a) may also be ligated to a cut vector. Advantageously this allows for the subsequent analysis and utilisation of the assembled DNA molecules. Thus according to a further aspect of the invention, there is provided a method of generating a library of DNA molecules of varying length and sequence in a desired orientation in a vector comprising the steps of:

a1) cutting a double-stranded DNA vector molecule with a first restriction enzyme.
a2) adding to the cut vector molecule a mixture of double-stranded DNA molecules, each of said molecules having 5' and 3' ends which correspond to the cleavage products of different but compatible restriction enzymes, one of said restriction enzymes being said first restriction enzyme,
b) allowing ligation to take place,
c) cutting the ligated DNA molecules with at least said first restriction enzyme such that molecules that are ligated in an incorrect orientation in the vector are cut out of the vector, and optionally
d) repeating steps (a2) to (c) to leave a library of DNA molecules of varying length and sequence in a desired orientation in a vector.

For each of description of the invention, each component of the mixture of double-stranded DNA molecules initially present at the start of the method will be referred to hereinafter as a "sequence block" (SB) unless stated otherwise. Each SB will in general be naturally occurring or synthetic DNA. The size of each SB is advantageously not crucial and may be varied widely as desired, for example from a few bases up to and beyond 10 Kb in length. Each end of a SB comprises half a restriction enzyme site and may be blunt-ended or preferably single-stranded thereby forming a cohesive end. Each half-size of each SB is compatible with the other. Particular sites include those equivalent to the half-sites obtainable by cutting with the restriction enzymes described hereinafter. Additionally, the SB may contain a recognition site for a restriction enzyme, which is preferably distinct from any recognition site capable of being formed by the half-sites of the SB.

Where desired the SB may define a specific motif. The motif may be biologically functional at the protein or at the nucleic acid level. In the latter case the motif may represent, for example, a promoter element, a binding motif for a regular or inhibitor protein, a response element, an enhancer element, a nuclease size, a hairpin motif or a spacer or linker domain that is required for the correct assembly of the double-stranded nucleic acid molecule.

In the case of an SB encoding a motif with a biological function as part of a portion, the motif may be a binding domain, especially for example a SH2 or SH3 domain, and a SH2 or SH3 binding domain, a dimerisation domain, a signalling sequence (such as an immunoglobuilin tyrosine based activation motif; ITAM), a recognition site for an enzyme, an immunoglobulin domain or fragment thereof, an epitope, a transmembrane domain, a catalytic domain, a regulatory domain, or α helical motif or other structural or functional domain. Particular examples of such domains will be readily clear to the man of skill in the art.

Each SB in the starting mixture may be generated by any convenient method, for example by PCR cloning from naturally occurring complementary DNA sources and subsequent cutting with appropriate restriction enzymes (see for example those described below). This allows the selection of any naturally-occurring sequence module of interest, of almost any length. More usually, the SBs may be generated by annealing two synthetic strands of nucleic acid (oligonucleotides) so that the 5' end and the 3' end form two appropriate overhangs. Combinations of these two approaches may be applied.

Restriction enzymes for use in the methods according to the invention recognise symmetric double-stranded DNA sequences and cleave within the sequences leaving a 3'-hydroxyl on one side of the cut and a 5' phosphate on the other. Depending on the type of restriction enzyme, a fragment with either a cohesive end (having a 5' or 3' single-stranded overhang) or a blunt-ended end (no single-stranded overhand) is produced. Cohesive DNA fragments can be ligated to other DNA fragments if their single-stranded overhangs are compatible. Depending on the sequence of the cleavage product of each fragment that is ligated together, either the original recognition sequence, a new recognition sequence or even no recognition sequence may be formed on ligation. Different restriction enzymes that produce compatible overhangs, which may be ligated together such that the may or may not produce a recleavable ligation product, are termed "compatible restriction enzymes". When overhangs that have been generated by the same restriction enzyme religate together, they reform a recognition site for that enzyme.

In the method of the invention, compatible restriction enzymes that have a 6 base pair or longer recognition sequence are preferred, since such enzymes cut DNA infrequently. Assuming a 50% G-C content of the DNA, a restriction enzyme with a 6 base pair recognition sequence will cleave, on average, every $4^6$ (4096) base pairs in a given DNA sequence. Restriction enzymes that produce cohesive ends are preferred since they ligate much more efficiently.

One example of two compatible restriction enzymes that form cohesive ends on digestion is the BamHI/BclI pair. These enzymes produce overhangs that may be ligated to each other, but which form a ligation product that is not cleavable by either enzyme. In fact, the ligation product may be cleaved by the unrelated enzymes AlwI and DpnI.

Preferred restriction enzymes that form cohesive ends are: AvaI, BamHI, BclI, BglII, BstEI, BstBI, BstYI, EcoRI, MluI, NarI, NheI, NotI, PstI, PvuI, SacI, SalI, SpeI, StyI, XbaI, XhoI and XmaI. Most preferably, the compatible set BglII, BamHI and BclI is used. Preferred enzymes that form blunt ends are EcoRV, FspI, NaeI, NruI, PvuII, SmaI, SnaBI and StuI.

It is envisaged that more than one pair of restriction endonucleases that are different but produce compatible cleavage products, may be employed in the method of the invention.

The recognition sites of these enzymes, the sites with which they are compatible, and the cleavable products are listed in categories of most restriction enzyme suppliers, for example the New England Biolabs catalogue.

In the present invention, compatible restriction enzymes are selected on the basis of the amino acid sequence that is desired, the necessity to maintain the reading frame of the protein sequence, and the rarity with which the enzymes cut the chosen DNA sequence. Also relevant is whether during subsequent steps of the process, it will be desirable to recleave at the ligation point.

Where in a method according to the invention the SBs are ligated to a cut vector, the latter may be any double-stranded DNA vector which has been cut with a restriction enzyme, for example, selected from those described above. The vector may contain such features necessary to enable the vector to be grown, maintained and selected in a host cell, including prokaryotic, yeast and higher eukaryotic e.g. mammalian cells.

The vector may be an expression vector and, in this event, may comprise an appropriately-positioned promoter, polyadenylation signal and transcription termination sequence, as well as features to allow expression of a protein encoded by a combination of SBs, such as a ribosome binding site and signal sequences. Enhancers, introns with functional splice donor and acceptor sites, and leader sequences may also be included in an expression construct, if so desired. Expression constructs are normally maintained in a replicon, such as an episomal element (e.g. plasmid) capable of stable maintenance in a host, such as mammalian cells or bacteria. For further details, see *Biological Regulation and Development: Gene Expression* (ed. R. F. Goldberger) and *Molecular Cloning: A Laboratory Manual* (Sambrook et al. (1989)).

Suitable vectors for use in the invention are widely available, for example from commercial suppliers such as Clontech Laboratories, Inc., Palo Alto, USA and Stratagene, La Jolla, USA, and may be modified as desired using conventional techniques.

Particularly suitable vectors for use in processes according to the invention include viral vectors such as retroviral and adenoviral vectors in mammalian cells.

In general, a desirable feature of the vector is that, once the SBs have been assembled into the vector and analysed, the SB combination(s) of choice may be transferred from the cloning vector and inserted into alternative vectors that allow the function or structure of the assembled SBs to be assessed. In most instances, this will be achieved by utilising a unique restriction site that is recognised by an enzyme that does not cut at any site in the sequence of the assembled SBs.

A vector of choice is a cloning cassette system derived from pBluescript SK+ (Stratagene). This vector is a modification of the cassette system described in International Patent Specification WO97/23613, the contents of which are incorporated herein in their entirety.

Where desired, the process according to the invention may be adapted to use a solid phase. Thus, according to a further aspect of the invention there is provided a method of generating a library of DNA molecules of varying length and sequence in a desired orientation of a solid phase comprising the steps of:

a1) providing a solid phase to which is attached a first double-stranded DNA molecule which has an end corresponding to the cleavage product of a first restriction enzyme;

a2) adding to said solid phase a mixture of double-stranded DNA molecules, each of said molecules having 5' and 3' ends which correspond to the cleavage product of a different but compatible restriction enzyme, one of said restriction enzymes being said first restriction enzyme;

b) allowing ligation to take place, wherein ligation of said double-stranded DNA molecules in a correct orientation generates a molecule that is not cut by either of said restriction enzymes, whereas ligation in an incorrect orientation retains at one or more ligation points a restriction site that is recognised by one of said restriction enzymes; and c) cutting the ligated DNA molecules with one or both of said restriction enzymes such that only molecules that are ligated in an incorrect orientation are cut.

The solid phase may comprise any solid matrix to which a DNA molecule may be attached, for example a synthetic bead, column, or any other solid surface. Suitable methods of attachment of DNA molecules to a solid phase are known in the art, such as, for example by biotin capture (Sterky F., et al 1998, Journal of Biotechnology 60, 119–125) and by digoxigenin/anti-digoxigenin interaction (Ioannon, P. and Christopoulos, T. 1998, Analytical Chemistry 70, 698–702).

The methods according to the invention employ standard DNA ligatation reactions and restriction enzyme digestion to generate a DNA library. Such techniques are well-known and routinely practised, and are described for example in laboratory manuals such as "Molecular Cloning" [Maniatis et al., Cold Spring Harbour Laboratory, New York, 1998]. Suitable ligases, e.g. T4 DNA ligase, and necessary cofactors such as ATP, are commercially available and may be used according to the manufacturer's instructions. Similarly, restriction enzymes, such as those described above are commercially available and may be used as instructed by the supplier.

The ligation step in each method may be controlled by manipulation of SB concentration, incubation time and/or temperature to determine the degree of ligation. For maximum efficiency the ligation conditions, such as SB concentrations, may need to be determined empirically, for example by titration, for any particular application.

Where desired ligated SBs may be purified from other components of the ligation reaction, such as enzymes and ATP, using standard separation procedures, for example, by gel exclusion and other size fractionation techniques.

Of course, as will be apparent to the skilled artisan, any of the nucleic acids generated using the methods of the present invention may be mutagenised in accordance with standard techniques as describe, for example, in *Molecular Cloning: a Laboratory Manual;* 2nd edition, (Sambrook et al., 1989, Cold Spring Harbor Laboratory Press) or in *Protein Engineering; A practical approach* (edited by A. R. Rees et al., IRL Press 1993). A particularly suitable method for introducing mutations within individual SBs is described below. This method allows the introduction of random mutations at a specific site (or sites) within a SB.

This is achieved through the use of substantially complementary oligonucleotides, one or both of which is degenerate. These oligonucleotides are annealed, ligated into a suitable vector and then transformed into a suitable host. Mutations may thus be introduced at the sites of degeneracy; the precise mutation introduced will depend on the degree of degeneracy at a particular nucleotide position and the operation of the mismatch repair system of the host organism. This will repair any nucleotides that are mismatched between the substantially complementary oligonucleotide pairs during DNA replication, as the cells grow and divide.

Thus, the method of the invention may employ at least one mutant double-stranded DNA molecule, which has been generated by annealing substantially complementary oligonucleotides as described above, the sequences of which are based on a parent nucleic acid, to form a plurality of double-stranded DNA molecules, ligating said plurality of double-stranded DNA molecules with vector, transforming the modified vector molecules into a host cell, culturing said transformed cell under conditions suitable for growth and cell division and isolating mutated DNA from the host cell.

The oligonucleotides are preferably based on a parent nucleic acid. Such parent nucleic acid may encode a polypeptide (this aspect of the invention, where an SB encodes a string of amino acids is described below in more detail).

Mutations may be introduced by annealing complementary oligonucleotides, only one of which is degenerate. Alternatively they may be introduced by annealing complementary oligonucleotides, both of which are degenerate, either at corresponding, or at different, nucleotide positions.

More than one mutation may be introduced into each SB. However, it will be appreciated that there will be a maximum number of mutations that can be introduced at any one time. This number will depend on the length of the oligonucleotide and other factors that govern efficient annealing. However, we have found that the method works satisfactorily when an oligonucleotide exhibits degeneracy at a ratio equal to, or less than 1 degenerate nucleotide in every 5 nucleotides. This ratio is calculated as an average over the entire length of the oligonucleotide, and is meant to be used only as guide when designing a degenerate oligonucleotide, as it may be possible to increase the amount of degeneracy in certain circumstances.

In some instances, it may be desirable to cluster degeneracy in, for example, groups of three adjacent nucleotides. Clustering degeneracy in such groups of three is particularly useful if one wishes to effect change in the amino acid sequence that a particular SB encodes. Thus, an individual codon may be altered by making 1 out of 3, 2 out of 3 or all 3 adjacent nucleotides degenerate. It will be clear to the skilled man that whilst the number of nucleotides in a degenerate cluster may exceed three, the mismatch repair system of the host organism, into which the annealed oligonucleotides will be introduced, will only tolerate and repair a maximum number of unpaired nucleotides before invoking other repair mechanisms, e.g. excision of the unpaired region of DNA.

Whilst the method of mutagenesis allows one to target precisely which nucleotide(s) is mutated, the nature of the mutation will be random due to the degeneracy of the oligonucleotide at the site of mutations. It may be desirable to bias this mutation away from (or towards) a particular nucleotide base, for example, to reduce the probability of introducing a stop codon. This can be achieved by limiting the degree of degeneracy created at a given position within the oligonucleotide. One example of this limited degeneracy wold be where only C, G or T (and not A) are present at a particular position. It will be clear to the skilled reader that any desired bias may be introduced in this manner. Alternatively, if the degeneracy of the oligonucleotide at a given position is maximal (i.e. all four nucleotide bases or inosine are present at the desired sit of mutation), the mutation will be random.

The conditions that are required for annealing degenerate oligonucleotides will, in general, be similar to those described herein in the examples. However, it will be appreciated by the skilled reader that these conditions may vary and may be dependable on factors such as length of oligonucleotide, the percentage of nucleotides that are degenerate, and the percentage GC content. Annealed oligonucleotides will then be ligated with any suitable vector and transformed (for example, for calcium chloride transformation, electroporation or any other method that is well known in the art) into a suitable host organism, preferably bacteria or yeast. The host organism will then be cultured under conditions suitable for cell growth and maintenance of the vector, examples of which are readily available in the art, see for example, Sambrook et al., (*Molecular cloning: a laboratory manual.* 2nd edition. Cold Spring Harbour Press, N.Y.) and Glover (*DNA cloning: a practical approach, Volume II: Expression systems.* IRL press).

The methods of the invention may be repeated in iterative steps, for example, to incrementally increase in size and complexity the DNA molecules generated. For example, a library of molecules generated by a first round may itself be isolated and the isolated molecules used in a subsequent round. In this fashion, the number and type of motifs in the molecule may gradually be increased. Such iterative steps are of particular value for the generation of a selection of polypeptide species, each comprised of a different combination of protein modules. After each round of combination, the DNA molecules generated may be analysed as described below and promising candidate DNA molecules may then be selected and used in the next of the method.

In general, the method according to the invention allows the production of DNA libraries of any desired size and diversity. Particular libraries include those, for example, in which the DNA has been rationally designed. Thus, SBs of a predetermined length may be incorporated into a cut vector in sequential steps. This will be particularly advantageous when the DNA is intended to encode a multifunctional polypeptide sequence. For instance, in the Examples described herein relating to the construction of chimeric receptor sequences, the individual modules or domains that constitute the protein must be ordered appropriately, for example: binding components, extracellular spacer, transmembrane component, signalling component. Therefore, the individual SBs should be inserted in this order. Insertion in the correct orientation can be checked by restriction analysis or by nucleic acid sequencing.

In another example, the method allows the production of libraries generated from the random combination of SBs. In this method, a ligation reaction is carried out in which a large number of different SB components are employed, any of which may insert in either orientation. Depending upon the ligation reaction conditions, for example as described above, a large number of different SB combinations is possible. Strings of multiple ligated SBs are then restricted with both the SB 5' restriction enzyme and the SB 3' restriction enzyme, to destroy combinations that contain one or more SBs in the incorrect orientation, prior to insertion of the assembled blocks into a cloning vector.

In the above examples and in general selective order of ligation of SBs, of either random or pre-determined length may be controlled by the selective use of kinases and phosphatases to add or remote phosphate groups from some or all of the SB components. As will be clear to the skilled artisan, a 5' terminal phosphate group must be donated by the ligating species in order that ligase-directed ligation is possible. In most instances, the vector should be phosphatased so as to prevent its self-ligation.

Thus according to a further aspect of the invention there is provided a DNA library and each nucleic acid component thereof generated by the method according to any one of the above-described aspects of the invention. The invention also provides a host cell transformed or transfected by such nucleic acid molecules and protein molecules expressed from said nucleic acid. Thus, the method of the invention also provides for the generation of a library of protein or polypeptide molecules.

The method of the invention is ideally suited to the generation of novel peptide or polypeptide compounds that are either wholly or partly derived from a combination of motifs, modules or domains. Such novel peptides, polypeptides, and indeed any protein library, may be expressed in a host cell(s), following transformation of the host with a nucleic acid (or library of nucleic acids) generated by the method of the invention. This may be achieved by culturing host cells under conditions that are well known in the art to be suitable for expression of a polypeptide from a nucleic acid (see for example: *Molecular Cloning: a Laboratory Manual:* 2nd edition, Sambrook et al., 1989, Cold Spring Harbor Laboratory Press; *DNA cloning: a practical approach, Volume II: Expression systems,* encoded by D. M. Glover IRL Press, 1995; *DNA cloning: a practical approach, Volume IV: Mammalian systems,* edited by D. M. Glover IRL Press, 1995). Desirable peptide/polypeptide products may then be identified through any suitable screening process, and isolated, if required, by standard protein purification techniques that are well known in the art.

In this embodiment of the invention, the SBs are designed so as to encode an in-frame string of amino acids when the SBs are linked together in the correct orientation. In a preferred embodiment of the invention, the SBs are designed so that a stop codon is formed by the linkage of any two SBs in an incorrect orientation.

In the case of insertion of one or more SBs into a vector to express a polypeptide, the vector can be designed so that a stop codon is present after insertion of the laser SB in the correct orientation. Preferably, the vector will have stop codons in all reading frames.

In the case of peptides, the SBs will encode short lengths of amino acid sequence, such as antigenic epitopes or signal sequences. However, the SBs may be significantly longer. Entire proteins may be assembled from component domains by the combination of SBs in either a random or a rational order. For example, many proteins are composed of domains that are identifiable by the presence of known consensus sequences or a prevalence of certain amino acid residues.

Binding proteins such as antibodies are examples of such proteins, being composed of constant and variable domain. Receptors are also usually composed of known domain structures, such as an extracellular binding component for recognition of ligand, a transmembrane region, a dimerisation or oligomerisation domain, linker domains, signalling domains and other intracellular domains. Combinations of synthetic and natural sequences can also be constructed. In this respect, spacer and linker domains may be used to maintain the steric configuration of the molecule, as and when appropriate for optimisation of function.

Other domains suitable for use in the invention may be derived from sources that will be clear to those of skill in the art and will include enzymatic effector domains such as protease, kinase or phosphatase domains.

Suitable applications for peptides formed by the combination linkage of encoding SBs include many immunological applications. Most linear epitopes are fairly short in length, often comprising no more than 6–10 amino acid residues. It is envisaged that these epitopes may be combined to generate long stretches of sequence containing a number of different epitopes. Such a molecule might find application as a component of a vaccine, for example, if each of the epitopes is capable of eliciting a separate immune response. For example, such a polyepitope peptide might contain known epitopes from bacterial pathogens that cause disease such as tetanus, cholera and diphtheria. Other epitopes that selectively stimulate populations of the immune system might be used, such as carrier peptides comprising epitopes recognised by T helper cells.

Short stretches of polypeptide comprising a number of peptides encoded by SBs may also be inserted into whole proteins or protein domains. For example, it may be desirable to include a plurality of signalling sequences into an existing protein. In this event, the assembled SB component would be inserted in-frame into the appropriate site of an existing nucleic acid sequence or gene. As exemplified below, one example of such an application is the creation of a synthetic signalling component from the assembly of multiple individual signalling motifs that have been derived from different naturally-occurring signalling regions. This ready-assembled component can then be inserted into a specific site in the sequence of a protein so as to confer on that protein the functional properties of each signalling motif.

Many similar applications may be envisaged, as will be clear to those of skill in the art.

As has been mentioned above, in one embodiment, the method of the present invention allows the design of nucleic acid molecules derived from a plurality of SBs that do not necessarily encode proteins, but which constitute regulatory elements that affect the rate of transcriptional or translational events. Each individual SB may encode an element such as a promoter element, a binding motif for a regulator or inhibitor protein, a response element, an enhancer element, a nuclease site, a hairpin motif, or any other element of a nucleic acid which may be transformed from its natural position in a gene and used in a different context without losing its function. For example, it may be desirable to create an improved transcriptional element to increase the transcription of a gene or to make such transcription dependent upon the presence of a particular activator or inhibitor compound.

Analysis of the DNA molecules that have been generated by the assembled SBs which have been produced in accordance with the present invention, may be by any suitable transcription or translation system. For example, when the method of the invention is being used to design an improved or modulated promoter or other regulatory element affecting the levels of transcription, the analysis system may be a reporter plasmid, in which the assembled SBs are inserted upstream of an unrelated reporter gene so as to regulate their expression of the encoded reporter protein. Suitable reporter genes may be luciferase, β-galactosidase, alkaline phosphatase or green fluorescent protein (GFP).

An efficient promoter will give a high level of transcription that will be reflected in the levels of translated protein. Furthermore, the effect of an inhibitor or of an activator compound may be assessed by allowing transcription to take place in the presence of a suitable amount of that compound. Similarly, when the method of the invention is being used to generate DNA encoding a functional protein, the contents of any library may be assessed using an appropriate expression system with a suitable assay to screen for the desired, expressed, functional protein, for example, as described in the Examples herein.

The invention will now be described in further detail with specific reference to chimeric receptor molecules generated by the combination of SBs in a pBLUESCRIPT-based system. It will be appreciated that variation may be made from these specific Examples without departing from the scope of the invention.

All documents cited herein are incorporated by reference.

BRIEF DESCRIPTION OF THE FIGURES

FIG. 1: Schematic diagram showing system for assembly of SBs.

FIG. 3: Sequence of cloning cassette.

FIG. 4: Oligonucleotide sequences for chimeric receptor construction.

FIG. 5: Predicted amino acid sequence of SBs.

FIG. 6: Level of expression and degree of activation of chimeric receptors containing synthetic signalling components by surface-bound antigen.

FIG. 7: Activation of chimeric receptors containing synthetic signalling components by surface-bound antigen.

FIGS. 8–10: Activation of chimeric receptors containing synthetic signalling components by surface-bound antigen.

EXAMPLES

Figure 2:
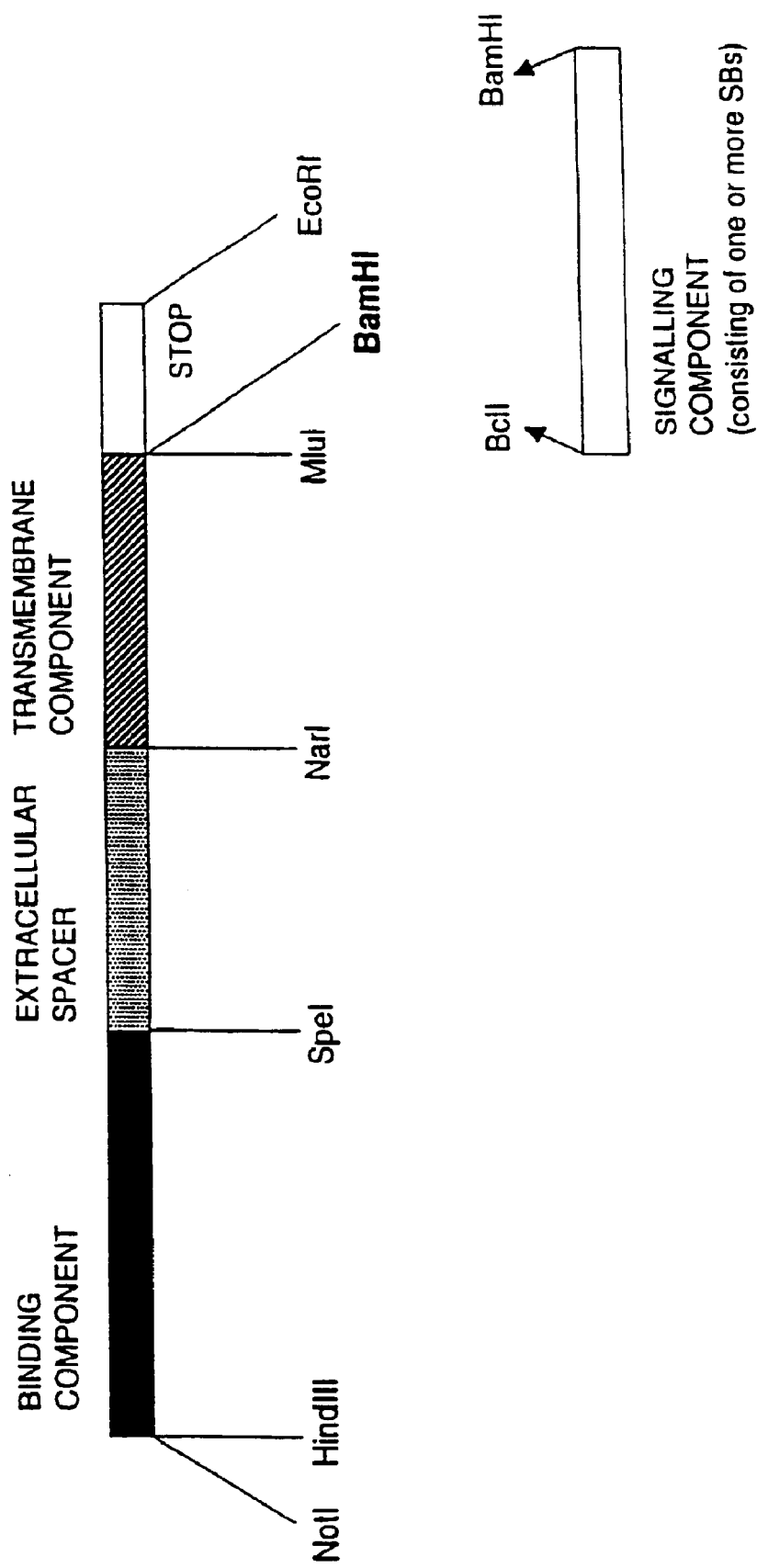
FIG. 2: Cloning cassette for construction of chimeric receptors with synthetic signalling components.

In these examples, we aim to construct a synthetic signalling component, from individual blocks of sequence, that is more potent than a naturally occurring signalling region for use in chimeric receptors. The individual sequence blocks are designed to include predicted signalling motifs from different naturally occurring signalling regions.

These sequence blocks (SBs) are constructed by annealing two synthetic strands of DNA (oligos) so that the 5' end forms a Bcl I overhang and the 3' end forms a BamH I overhang. Both these restriction site overhangs are compatible with a BamH I site in the cloning vector. Insertion of the SB in the correct orientation destroys the 5' BamH I site and retains a 3' BamH I site, allowing subsequent 3' insertion of SB(s). Insertion of the SB in the wrong orientation retains a 5' BamHI site and generates a 3' stop codon (FIG. 1). In this example the SBs have 5' and 3' phosphate groups and the BamH I site in the construction vector (FIG. 2) has its phosphate groups removed to prevent vector re-ligation in the absence of insert ligation.

Example 1

Construction of the Cloning Vector, pHMF393

To facilitate construction of chimeric receptors with different binding, extracellular spacer, transmembrane and signalling components, a cloning cassette system was devised in pBluescript SK+ (Stratagene). This is a modification of our cassette system described in International Patent Specification No. WO 97/23613.

This new cassette system is shown in FIG. 2. The binding component has 5' Not I and Hind III restriction sites and a 3' Spe I restriction site. The extracellular spacer has a 5' Spe I site (Tbr, Ser) and a 3' Nar I site (Gly, Ala). The transmembrane component has a 5' Nar I site (Gly, Ala) and 3' Mlu I (Thr, Arg) and BamHI sites (Gly, Ser). The signalling component may be cloned into the BamHI site. Following this BamH I site there is a stop codon for transcription termination and there is an EcoRI site situated 3' of this for subsequent rescue of whole constructs.

To generate this cassette, a 200 bp fragment was PCR assembled using oligos: S0146, A6081, A6082 and A6083 (FIG. 4). This fragment starts with a SpeI site and consists of the extracellular spacer h.CD28, the human CD28 transmembrane region, a stop codon and finishes with an EcoRI site (see FIG. 3). This PCR fragment was then restricted with SpeI and EcoRI and substituted for the same fragment in our previously described cloning cassette system to join the binding component (International Patent No. WO 97/237613 FIG. 2).

This cloning vector termed pHMF393 contains P67scFv/h.CD28/CD28TM and forms the base vector molecule into which synthetic signalling regions were built.

Example 2

Construction of Sequence Blocks (SBs)

Each sequence block was generated by annealing two oligos such that they have single-stranded overhangs forming half a Bcl I site at the 5' end and half a BamH I site at the 3' end. Oligos were annealed at a concentration of 1 pmole/μl in a buffer consisting of: 25 mM NaCl, 12.5 mM Tris-HCl, 2.5 mM MgCl$_2$, 0.25 mM DTE, pH 7.5 by heating in a boiling water bath for 5 minutes and then allowing the bath to cool slowly to room temperature.

The predicted amino acid sequences of these examples of SBs are shown in FIG. 5
1) SB1
This sequence is based on the first ITAM of human TCR ζ and was constructed by annealing oligos A8816 and A8817 (FIG. 4). Both these oligos have a 5' phosphate group.

2) SB2

This sequence is based on the second ITAM of human TCR ζ and was constructed by annealing oligos A8814 and A8815 (FIG. 4). Both these oligos have a 5' phosphate group.

3) SB3

This sequence is based on the third ITAM of human TCR ζ and was constructed by annealing oligos A8812 and A8813 (FIG. 4). Both these oligos have a 5' phosphate group.

4) SB 4

This sequence is based on the ITAM of the γ chain of human FcεR1 and was constructed by annealing oligos A8810 and A8811 (FIG. 4). Both these oligos have a 5' phosphate group.

5) SB4*

This sequence was originally generated in error by mis-annealment of the above oligos but was subsequently made by annealing oligos A8810B and A8811B (FIG. 4). Both these oligos have a 5' phosphate group.

6) SB5

This sequence is based on the ITAM of the β chain of human FcεR1 and was constructed by annealing oligos A9000 and A9001 (FIG. 4). Both these oligos have a 5' phosphate group.

7) SB6

This sequence is based on the ITAM of the γ chain of human CD3 and was constructed by annealing oligos A9002 and A9003 (FIG. 4). Both these oligos have a 5' phosphate group.

8) SB7

This sequence is based on the ITAM of the δ chain of human CD3 and was constructed by annealing oligos A9004 and A9005 (FIG. 4). Both these oligos have a 5' phosphate group.

9) SB8

This sequence is based on the ITAM of the ε chain of human CD3 and was constructed by annealing oligos A9006 and A9007 (FIG. 4). Both these oligos have a 5' phosphate group.

10) SB9

This sequence is based on the ITAM of human CD5 and was constructed by annealing oligos A9008 and A9009 (FIG. 4). Both these oligos have a 5' phosphate group.

11) SB10

This sequence is based on the ITAM of human CD22 and was constructed by annealing oligos A9010 and A9011 (FIG. 4). Both these oligos have a 5' phosphate group.

12) SB11

This sequence is based on the ITAM of human CD79a and was constructed by annealing oligos A9012 and A9013 (FIG. 4). Both these oligos have a 5' phosphate group.

13) SB12

This sequence is based on the ITAM of human CD79b and was constructed by annealing oligos A9014 and A9015 (FIG. 4). Both these oligos have a 5' phosphate group.

14) SB13

This sequence is based on the ITAM of human CD66d and was constructed by annealing oligos A9016 and A9017 (FIG. 4). Both these oligos have a 5' phosphate group.

15) SB28

This sequence is based on the co-stimulation motif of human CD28 and was constructed by annealing oligos A9018 and A9019 (FIG. 4). Both these oligos have a 5' phosphate group.

16) SB29

This sequence is based on the co-stimulation motif of human CD154 and was constructed by annealing oligos A9020 and A9021 (FIG. 4). Both these oligos have a 5' phosphate group.

Example 3

Construction of Mutated Sequence Blocks

Exemplification of mutation of SB1.

SB1, based on the first ITAM of TCR ζ, has the naturally occurring amino acid sequence of: QNQLYNELNLGR-REEYDVLDKRRGRDPEM (SEQ ID NO. 3). Degenerate oligonucleotides (D7001 and D7002) were designed to alter the three amino acid residues following each of the ITAM-defining tyrosine residues (ie, the six residues highlighted in bold, above). The oligonucleotides were designed such that any residue cold be introduced at the first two positions following the tyrosine, but only leucine, or isoleucine, or valine would be introduced at the third position. Thus, mutated SBs with the following sequence would be generated (where X is any amino acid):

```
              I              I
GSQNQLYXXLNLGRREEYXXLDKRRGRDPEMGS  (SEQ ID NO.63)
              V              V
```

Degenerate oligonucleotides D7001 and D7001 were annealed at a concentration of 1 pmole/μl in a buffer consisting of 25 mM NaCl, 12.5 mM Tris.HCl, 2.5 mM MgCl$_2$, 0.25 mM DTE, pH 7.5, by heating in a boiling water bath for 5 minutes and then allowing them to cool slowly to room temperature. Approximately 1 pmole of annealed oligonucleotides were mixed with approximately 1 ng of BamHI-digested pBluescript, T4 DNA ligase and ATP in a 10 μl reaction volume and ligation performed under the manufacturer's recommended conditions. Competent *Escherichia coli,* strain XL1-Blue, were transformed with 2 μl of ligation reaction, and plated onto LB agar containing ampicillin. Ampicillin resistant colonies were picked and grown up in L-broth containing ampicillin, and plasmid DNA prepared. The presence and sequence of any insert in the pBluescript vector was confirmed by sequencing with oligonucleotides corresponding to regions 5' and 3' to the BamHI site in the vector. Representative examples of mutant SBs generated using this method with degenerate oligonucleotides D7001 and D7002 are given as SBW1A, SBW1B, SBW1C and SBW1D in Table 1.

TABLE 1

Examples of mutant sequence blocks generated using degenerate oligonucleotides D7001 and D7002

| Sequence Block | Amino Acid Sequence | Sequence ID No. |
| --- | --- | --- |
| SBW1A | GSQNQLYPPLNLGRREEYRPLDKRRGRDPEMGS | 60 |
| SBW1B | GSQNQLYGGLNLGRREEYGKIDKRRGRDPEMGS | 61 |

TABLE 1-continued

Examples of mutant sequence blocks generated using degenerate oligonucleotides D7001 and D7002

| Sequence Block | Amino Acid Sequence | Sequence ID No. |
|---|---|---|
| SBW1C | GSQNQLYGAVNLGRREEYTGVDKRRGRDPEMGS | 62 |
| SBW1D | GSQNQLYTGINLGRREEYGTVDKRRGRDPEMGS | 63 |

Example 4

Construction of Chimeric Receptors with Synthetic Signalling Regions by Sequential Addition The vector, pHMF393 was digested with the restriction enzyme BamH I under the manufacturer's recommended conditions and then treated with alkaline phosphatase for 10 minutes at 37° C. in the same buffer. The linearised vector fragment was eluted from an agarose gel and purified. Approximately 1 ng of vector fragment was ligated to approximately 1 pmole of SB or mixture of SBs using T4 ligase and ATP under the manufacturer's recommended conditions in a 10 µl reaction. 2 µl of the ligation reaction was transformed into XL-1 blue competent E. coli and plated onto L-broth/Ampicillin plates. Ampicillin resistant colonies were picked and grown up in L-broth containing Ampicillin, and plasmid DNA prepared. Correct orientation of the inserted SB was established by digesting the DNA with BamH I and an enzyme within the Vector (Nar I). Optionally before picking, colonies were screened for the presence of inserted SBs by PCR using oligos corresponding to regions 5' and 3' to the BamH I site in the vector. Positive colonies were then grown up in L-broth containing Ampicillin and plasmid DNA prepared. Correct orientation of the inserted SB was established by digesting the DNA with BamH I and an enzyme within the Vector (Nar I).

Correct plasmids were then digested with BamH I, treated with alkaline phosphatase, gel purified and ligated to an SB, or mixture of SBs, as described above to insert a second SB. Colonies were screened again in the same way to find vectors with a second SB in the correct orientation. These vectors were then put through further rounds of digestion, purification, ligation and screening, as desired, to generate the required number of SBs in the correct orientation in a vector.

Specific Example: (see Table 2)
P67/h.CD28/CD28TMSB2.SB1.SB3.SB1 (pHMF369) was constructed by the following steps of sequential addition:
  ligation of vector pHMF393 to SB2 to generate pHMF403
  ligation of vector pHMF403 to SB1 to generate pHMF410
  ligation of vector pHMF410 to SB3 to generate pHMF432
  ligation of vector pHMF432 to SB1 to generate pHMF469.

Example 5

Construction of Chimeric Receptors with Synthetic Signalling Regions by Multiple Addition Construction of synthetic signalling regions with random combinations of SBs by adding mixtures of more than one SB at a time was done by the following methods:

a) SBs were ligated to each other in the absence of vector and then digested with both Bcl I and BamH I to cut SBs ligated to each other in incorrect orientations. If a specific number of SBs were required, then the desired size fragments were gel eluted and purified; if not, the ligated SB fragments were purified from the restriction enzymes and then ligated to the digested, phsophatased and purified vector as in Example 3. Ampicillin-resistant colonies were then generated and screened as in Example 3 to select vectors with more than one SB in the correct orientation in a vector.

b) SBs were ligated to the digested, phosphatased and purified vector and then digested with both Bcl I and BamH I to cut Sbs ligated to each other and to the vector in incorrect orientations. Fragments larger than the unligated vector were gel purified and then ligated to recircularise. Ampicillin-resistant colonies were then generated and screened as in Example 3, to select vectors with more than one SB in the correct orientation in a vector.

c) SBs were ligated to the digested, phosphatased and purified vector at a ratio of SB to vector that favoured the insertion of multiple SBs; Ampicillin resistant colonies were then generated and screened as in Example 3 to select vectors with more than one SB in the correct orientation in a vector.

It was found that for maximum efficiency it was desirable to use method c and establish a titration of SB for each vector. A de-stimulation of colony number from vector only controls was a good indication of insertion of multiple SBs. It was also found to be more efficient to perform two rounds of ligation and screening for correct insertion of a low number of SBs rather than one round of ligation and screening for many SBs in the correct orientation. Statistically, adding 1 SB, 50% should be in the correct orientation; adding 2 SBs, 25% should be in the correct orientation but when 4SBs are added at one time only 6% of vectors would have all 4 SBs in the desired orientation.

In the case of multiple rounds of multiple insertion, mixtures of both vector and SBs were ligated to each other to increase diversity of the library produced.

Specific examples: (see Table 2)
P67/h.CD28/CD28TM/SB11.SB5.SB10.SB9 (pHMF537);
P67/h.CD28/CD28TM/SB4.SB7.SB10 (pHMF538);
P67/h.CD28/CD28TM/SB4.SB3 (pHMF539); and
P67/h.CD28/CD28TM/SB4.SB1 (pHMF540) were constructed by ligating a mixture of linearised and phosphatased vectors already containing one SB:
pHMF403,404,405,406,515 and 516 to a mixture of SBs: SB1,SB2,SB3,SB4,SB4*,SB5,SB6,SB7,SB8,SB9,SB10, SB11,SB12,SB13 and SB28.
P67/h.CD28/CD28TM/SB2.SB1.SB1 (pHMF529);
P67/h.CD28/CD28TM/SB2.SB4.SB5 (pHMF530);
P67/h.CD28/CD28TM/SB11.SB4*.SB3 (pHMF531); and P67/h.CD28/CD28TM/SB11.SB4*.SB10* (pHMF532) were constructed by ligating a mixture of linearised and phophatased vectors already containing two SBs: pHMF 408,410,412,518,519,520,521 and 522 to a mixture of SBs: SB1,SB2,SB3,SB4,SB4*,SB5,SB6,SB7, SB8,SB9,SB10,SB11,SB12,SB13 and SB28.

Example 6

Analysis of Receptors a) Construction of expression plasmids

The chimeric receptor constructs were subcloned from pBluescript KS+ into the expression vector pEE6hCMV.ne (C. R. Bebbington (1991), Methods 2, 136–145) on a HindIII to EcoRI restriction fragment. The expression vector with no chimeric receptor genes is used as a negative control in subsequent experiments.

b) Stable transfection into Jurkat E6.1 cells

The expression plasmids were linearised and transfected into Jurkat E6.1 cells (ECACC) by electroporation using a Bio-rad Gene Pulser. 10 μg of DNA per $2.5\times10^6$ cells were given two pulses of 1000V, 3 μF in 1 ml of PBS. Cells were left to recover overnight in non-selective medium before being selected and cultured in medium supplemented with the antibiotic G418 (Sigma) at 1.5 mg/ml. After approximately four weeks the cells were ready for analysis.

c) FACS analysis of surface expression

Approximately $5\times10^5$ Jurkat cells were stained with 1 μg/ml FITC labelled antigen, CD33 extracellular region. Fluorescence was analysed by a FACScan cytometer (Becton Dickinson).

d) IL-2 production analysis of function $2\times10^5$ cells were incubated at 37° C./8% $CO_2$ for 20 hours in 96 well plates with CD33 expressing HL60 target cells at an effector: target ratio of 1:1. Cell supernatants were then harvested and assayed for human IL-2 (R & D Systems Quantikine kit).

Example 7

Results

The library of synthetic signalling regions produced is listed in Table 2. These were constructed by the methods described in example 3 and example 4. All signalling regions were sequenced prior to analysis and some additional diversity of the library was found to arise from mis-annealment and recombination events and these are listed in the notes to Table 2.

This diversity library of synthetic signalling receptors were demonstrated to function specifically in response to antigen (see FIGS. 6 to 10).

TABLE 2

| pBluescript | Binding | Spacer | Trans-membrane | Signalling Region | EE6hCMVNE/Jurkat line | NOTES |
|---|---|---|---|---|---|---|
| pHMF403 | hP67scFv | h.CD28 | CD28 | SB1 | pHMF/J.434 | |
| 404 | hP67scFv | h.CD28 | CD28 | SB2 | 435 | |
| 405 | hP67scFv | h.CD28 | CD28 | SB4 | 436 | |
| 406 | hP67scFv | h.CD28 | CD28 | SB3 | 437 | |
| 407 | hP67scFv | h.CD28 | CD28 | SB1.SB1 | 438 | |
| 408 | hP67scFv | h.CD28 | CD28 | SB1.SB2 | 439 | |
| 409 | hP67scFv | h.CD28 | CD28 | SB1.SB3 | 440 | |
| 410 | hP67scFv | h.CD28 | CD28 | SB2.SB1 | 441 | |
| 411 | hP67scFv | h.CD28 | CD28 | SB2.SB3 | 442 | |
| 412 | hP67scFv | h.CD28 | CD28 | SB2.SB4 | 443 | |
| 427 | hP67scFv | h.CD28 | CD28 | SB1.SB4 | 444 | |
| 428 | hP67scFv | h.CD28 | CD28 | SB2.SB4* | 445 | 1 |
| 429 | hP67scFv | h.CD28 | CD28 | SB4.SB4* | 446 | 1 |
| 430 | hP67scFv | h.CD28 | CD28 | SB3.SB4* | 447 | 1 |
| 431 | hP67scFv | h.CD28 | CD28 | SB1.SB2.SB3 | 448 | |
| 432 | hP67scFv | h.CD28 | CD28 | SB2.SB1.SB3 | 449 | |
| 433 | hP67scFv | h.CD28 | CD28 | SB2.SB4.SB3 | 500 | |
| 469 | hP67scFv | h.CD28 | CD28 | SB2.SB1.SB3.SB1* | 475 | 2 |
| 470 | hP67scFv | h.CD28 | CD28 | SB2.SB1.SB3.SB2 | 476 | |
| 471 | hP67scFv | h.CD28 | CD28 | SB2.SB1.SB3.SB3 | 477 | |
| 472 | hP67scFv | h.CD28 | CD28 | SB2.SB1.SB3.SB4 | 478 | |
| 473 | hP67scFv | h.CD28 | CD28 | SB2.SB4.SB3.SB1 | 479 | 3 |
| 474 | hP67scFv | h.CD28 | CD28 | SB2.SB4.SB3.SB2 | 480 | 3 |
| 501 | hP67scFv | h.CD28 | CD28 | SB2.SB4.SB3.SB28 | 507 | 3 |
| 502 | hP67scFv | h.CD28 | CD28 | SB2.SB1.SB3.SB1*.SB28 | | |
| 503 | hP67scFv | h.CD28 | CD28 | SB2.SB4.SB3.SB2.SB28 | 508 | |
| 504 | hP67scFv | h.CD28 | CD28 | SB2.SB4.SB3.SB29 | 509 | |
| 505 | hP67scFv | h.CD28 | CD28 | SB2.SB1.SB3.SB1*.SB29 | | |
| 506 | hP67scFv | h.CD28 | CD28 | SB2.SB4.SB3.SB2.SB29 | 510 | 3 |
| 511 | hP67scFv | h.CD28 | CD28 | SB2.SB1.SB3.SB1* | 512 | 2 |
| 513 | hP67scFv | h.CD28 | CD28 | SB2.SB1.SB28 | 514 | |
| 515 | hP67scFv | h.CD28 | CD28 | SB11 | 523 | |
| 516 | hP67scFv | h.CD28 | CD28 | SB28 | | |
| 517 | hP67scFv | h.CD28 | CD28 | SB3'.SB4* | | 1.4 |
| 518 | hP67scFv | h.CD28 | CD28 | SB11.SB4* | 524 | |
| 519 | hP67scFv | h.CD28 | CD28 | SB3.SB3 | 525 | |
| 521 | hP67scFv | h.CD28 | CD28 | SB4*.SB1 | 527 | 1.5 |
| 522 | hP67scFv | h.CD28 | CD28 | SB4*.SB3 | 528 | 1 |
| 529 | hP67scFv | h.CD28 | CD28 | SB2.SB1.SB1 | 533 | |

TABLE 2-continued

| pBluescript | Binding | Spacer | Trans-membrane | Signalling Region | EE6hC MVNE/Jurkat line | NOTES |
|---|---|---|---|---|---|---|
| 530 | hP67scFv | h.CD28 | CD28 | SB2.SB4.SB5 | 534 | |
| 531 | hP67scFv | h.CD28 | CD28 | SB11.SB4*.SB3 | 535 | 1 |
| 532 | hP67scFv | h.CD28 | CD28 | SB11.SB4*.SB10* | 536 | 1.6 |
| 537 | hP67scFv | h.CD28 | CD28 | SB11.SB5.SB10.SB9 | 559 | |
| 538 | hP67scFv | h.CD28 | CD28 | SB4.SB7.SB10 | 560 | |
| 539 | hP67scFv | h.CD28 | CD28 | SB4.SB3 | | |
| 540 | hP67scFv | h.CD28 | CD28 | SB4.SB1 | | |
| 541 | hP67scFv | h.CD28 | CD28 | SB1.SB3 | | |
| 542 | hP67scFv | h.CD28 | CD28 | SB28.SB1 | 561 | |
| 543 | hP67scFv | h.CD28 | CD28 | SB11.SB7 | 562 | |
| 544 | hP67scFv | h.CD28 | CD28 | SB3.SB13 | 563 | |
| 545 | hP67scFv | h.CD28 | CD28 | SB28.SB4* | 564 | 1 |
| 547 | hP67scFv | h.CD28 | CD28 | SB2.SB1.SB2 | 565 | |
| 549 | hP67scFv | h.CD28 | CD28 | SB4*.SB3.SB3 | 567 | 1 |
| 550 | hP67scFv | h.CD28 | CD28 | SB1.SB2.SB9 | 568 | |
| 551 | hP67scFv | h.CD28 | CD28 | SB1.SB2.SB12 | 569 | |
| 552 | hP67scFv | h.CD28 | CD28 | SB4*'.SB1.SB1 | 570 | 1.5 |
| 553 | hP67scFv | h.CD28 | CD28 | SB3.SB3.SB4* | 571 | 1 |
| 554 | hP67scFv | h.CD28 | CD28 | SB4*.SB1.SB12 | 572 | 1 |
| 555 | hP67scFv | h.CD28 | CD28 | SB2.SB4.SB28 | 573 | |
| 556 | hP67scFv | h.CD28 | CD28 | SB3.SB3.SB7 | 574 | |
| 557 | hP67scFv | h.CD28 | CD28 | SB11.SB4*.SB10 | 575 | 1 |
| 558 | hP67scFv | h.CD28 | CD28 | SB1.SB4*.SB3 | 576 | 1 |
| 577 | hP67scFv | h.CD28 | CD28 | SB28.SB4*.SB2 | 589 | 1 |
| 578 | hP67scFv | h.CD28 | CD28 | SB28.SB1.SB3 | 590 | |
| 579 | hP67scFv | h.CD28 | CD28 | SB28.SB4*.SB4* | 591 | 1 |
| 580 | hP67scFv | h.CD28 | CD28 | SB28.SB1.SB28 | 592 | |
| 581 | hP67scFv | h.CD28 | CD28 | SB28.SB1.SB2 | 593 | |
| 582 | hP67scFv | h.CD28 | CD28 | SB28.SB1.SB13 | 594 | |
| 583 | hP67scFv | h.CD28 | CD28 | SB28.SB3* | 595 | |
| 584 | hP67scFv | h.CD28 | CD28 | SB28.SB13 | 596 | |
| 585 | hP67scFv | h.CD28 | CD28 | SB28.SB10 | 597 | |
| 586 | hP67scFv | h.CD28 | CD28 | SB28.534*.SB2.SB4 | 598 | 1 |
| 587 | hP67scFv | h.CD28 | CD28 | SB28.SB1.SB4" | 599 | 7 |
| 608 | hP67scFv | h.CD28 | CD28 | SB28.SB2 | 612 | |
| 609 | hP67scFv | h.CD28 | CD28 | SB11.SB2 | 613 | |
| 610 | hP67scFv | h.CD28 | CD28 | SB28.SB2.SB1 | 614 | |
| 611 | hP67scFv | h.CD28 | CD28 | SB28.SB2.SB4 | 615 | |

Notes to Table 2

1) SB4* is a single amino acid different from SB4, initially generated by mis-annealment of oligos but subsequently deliberately generated by annealing oligos A8810B and A8811B (see FIG. 4) due to enhanced activity.

SB4*: GSYEKSDGVYTGLSTRNQETYDTLKHEKPS (SEQ ID NO. 8)

2) SB1* is a truncated version of SB1 generated by a recombinant event during cloning.

SB4*: GSGQNQLYNELNLGRREEYDVALAK (SEQ ID NO. 4)

3) R to G change at the 5' end of SB3

4) A to T change at the 3' end of SB3

5) K to R change at the 5' end of SB4*

6) SB10* is a truncated version of SB10 with an altered 3' end.

SB10*: GSPPRTCDDTVTYSALHKRQVGDYENVI-PER (SEQ ID NO. 16)

7) S to L change at the 5' end of SB4 and a S to G change in the middle of SB4.

SB4": GLYEKSDGVYTGLGTRNQETYETLKHEK-PGS (SEQ ID NO. 9)

What is claimed is:

1. A method of generating a library of DNA molecules of varying length and sequence in a desired orientation comprising the steps of:
   a) providing a mixture of double-stranded DNA molecules, each of said molecules having 5' and 3' ends which are compatible to each other and are equivalent to the cleavage products of different but compatible restriction enzymes; and
   b) allowing ligation to take place, wherein ligation of said double-stranded DNA molecules in desired orientations generates molecules that are not cut by either of said restriction enzymes whereas ligation in undesired orientations generates molecules that retain at one or more ligation points a restriction site that is recognised by one of said restriction enzymes; and
   c) cutting the ligated DNA molecules with one or both of said restriction enzymes such that only molecules that are ligated in undesired orientations are cut, leaving a library of DNA molecules of varying length and sequence in a desired orientation.

2. A method of generating a library of DNA molecules of varying length and sequence in a desired orientation in a vector comprising the steps of:
   a1) cutting a double-stranded DNA vector molecule with a first restriction enzyme;
   a2) adding to the cut vector molecule a mixture of double-stranded DNA molecules, each of said molecules having 5' and 3' ends which are equivalent to the cleavage products of different but compatible restriction enzymes, one of said restriction enzymes being said first restriction enzyme;
   b) allowing ligation to take place;
   c) cutting the ligated DNA molecules with at least said first restriction enzyme such that molecules that are ligated in an incorrect orientation in the vector are cut out of the vector; and optionally
   d) repeating steps (a2) to (c); to leave a library of DNA molecules of varying length and sequence in a desired orientation in a vector.

3. A method of generating a library of DNA molecules of varying length and sequence in desired orientation on a solid phase comprising the steps of:
   a1) providing a solid phase to which is attached a first double-stranded DNA molecule which has an end that is equivalent to the cleavage product of a first restriction enzyme;
   a2) adding to said solid phase a mixture of double-stranded DNA molecules, each of said molecules having 5' and 3' ends which are the cleavage product of a different but compatible restriction enzyme, one of said restriction enzymes being said first restriction enzyme;
   b) allowing ligation to take place, wherein ligation of said double-stranded DNA molecules in a correct orientation generated a molecule that is not cut by either of said restriction enzymes, whereas ligation in an incorrect orientation retains at one or more ligation points a restriction site that is recognised by one of said restriction enzyme; and
   c) cutting the ligated DNA molecules with one or both of said restriction enzymes such that only molecules that are ligated in an incorrect orientation are cut, thus leaving a library of DNA molecules of varying length and sequence in a desired orientation.

4. The method according to claim 3 wherein said solid phase is a bead.

5. The method according to claim 1 wherein each double-stranded DNA molecule has single-stranded cohesive ends.

6. The method according to claim 2 wherein each double-stranded DNA molecule has single-stranded cohesive ends.

7. The method according to claim 3 wherein each double-stranded DNA molecule has single-stranded cohesive ends.

8. The method according to claim 5, wherein said mixture comprises at least a first and a second double-stranded molecule, wherein said first double-stranded DNA molecule contains a unique recognition site for a restriction enzyme that does not cut said second double-stranded DNA molecules to allow the subsequent insertion of the ligated DNA molecules into a vector.

9. The method according to claim 6, wherein said mixture comprises at least a first and a second double-stranded molecule, wherein said first double-stranded DNA molecule contains a unique recognition site for a restriction enzyme that does not cut said second double-stranded DNA molecules to allow the subsequent insertion of the ligated DNA molecules into a vector.

10. The method according to claim 7, wherein said mixture comprises at least a first and a second double-stranded molecule, wherein said first double-stranded DNA molecule contains a unique recognition site for a restriction enzyme that does not cut said second double-stranded DNA molecule to allow the subsequent insertion of the ligated DNA molecules into a vector.

11. The method according to claim 8 further comprising the step of cutting at said unique restriction site and inserting said ligated DNA molecule into a vector.

12. The method according to claim 9 further comprising the step of cutting at said unique restriction site and inserting said ligated DNA molecule into a vector.

13. The method according to claim 10 further comprising the step of cutting at said unique restriction site and inserting said ligated DNA molecule into a vector.

14. The method according to claim 2, further comprising the steps of:
   e) isolating correctly ligated DNA molecules;
   f) adding said isolated DNA molecule to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

15. The method according to claim 3, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

16. The method according to claim 6, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

17. The method according to claim 7, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

18. The method according to claim 9, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

19. The method according to claim 10, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

20. The method according to claim 12, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);
   and optionally,
   g) repeating steps e) and f); to leave a library of DNA molecules of varying length and sequence in a desired orientation.

21. The method according to claim 13, further comprising the steps of:
   e) isolating correctly ligated DNA molecules;
   f) adding said isolated DNA molecules to a further mixture of double-stranded DNA molecules, each of said molecules having 5' and 3' ends which are equivalent to the cleavage product of different but compatible restriction enzymes and repeating steps b) and c);

and optionally, g) repeating steps e) and f); to leave a library of DNA molecules of varying length and sequence in a desired orientation.

22. The method according to claim 1, further comprising the step of selecting the ligated DNA molecules for a desired length after step b and/or after step c).

23. The method according to claim 2, further comprising the step of selecting the ligated DNA molecules for a desired length after step b) and/or after step c).

24. The method according to claim 3, further comprising the step of selecting the ligated DNA molecules for a desired length after step b) and/or after step c).

25. A method according to claims 14–15, wherein the library of DNA molecules produced is subsequently cut with a third restriction enzyme and added to a further mixture of double-stranded DNA molecules, each of said molecules having 5' and 3' ends which are equivalent to the cleavage product of said third restriction enzyme and the cleavage product of a restriction enzyme that is different but compatible with said third restriction enzyme, ligation is allowed to take place, and the ligated DNA molecules are then cut with at least said third restriction enzyme, wherein molecules that are ligated in an incorrect orientation are cut out.

26. The method according to claims 1–3 wherein said mixture of double-stranded DNA molecules is mixture of annealed single-stranded oligonucleotides.

27. The method according to claim 26 wherein said annealed single-stranded oligonucleotides comprise 5' phosphate groups.

28. The method according to claim 26 wherein said annealed single-stranded oligonucleotides comprise at least one mis-matched base pair.

29. The method according to any of claims 1–3 wherein said mixture of double-stranded DNA molecules is generated by amplifying a DNA molecule using PCR and cutting with appropriate restriction enzymes.

30. The method according to any of claims 1–3 wherein said mixture of double-stranded DNA molecules is generated by cutting genomic or cDNA with appropriate restriction enzymes.

31. The method according to any of claims 1–3 wherein at least one of said double-stranded DNA molecules carries a mutation.

32. The method according to claim 31 wherein said double-stranded DNA molecule carrying a mutation has been generated by:

combining degenerate oligonucleotides under conditions that substantially complementary oligonucleotides anneal to form a plurality of double-stranded DNA molecules, ligating said plurality of double-stranded DNA molecules into a vector, transforming the modified vector molecules into a host cell, culturing said transformed cell under conditions suitable for growth and cell division and isolating said mutant double-stranded molecules from said host cell.

33. The method according to claim 32, wherein the sequence of at least one the degenerate oligonucleotides is based on a parent nucleic acid.

34. The method according to claim 33, wherein said parent nucleic acid encodes a polypeptide.

35. The method according to claim 32, wherein at least one of said complementary oligonucleotides exhibits degeneracy at a ratio equal to or less than 1 in every 5 nucleotides.

36. The method according to claim 32, wherein degeneracy is clustered in groups of 3 adjacent nucleotides, and/or any 2 out of 3 adjacent nucleotides, and/or any 1 out of 3 adjacent nucleotides.

37. The method according to claim 36, wherein said 3 adjacent nucleotides encode an amino acid of the polypeptide encoded by any one of the plurality of double-stranded DNA molecules, and/or an amino acid of the polypeptide encoded by the parent nucleic acid.

38. The method according to claim 32, wherein the degeneracy at one or more nucleotide positions is generated through the inclusion of at least two members selected from the group consisting of A, C, G, T, or I at the desired site of mutation.

39. The method according to claim 32, wherein each of a pair of substantially complementary oligonucleotides exhibits degeneracy at a corresponding position when the two oligonucleotides are annealed.

40. The method of any of claims 2–3, wherein said mixture is produced by a method comprising:

a) providing a mixture of double-stranded DNA molecules, each of said molecules having 5' and 3' ends which are compatible to each other and are equivalent to the cleavage products of different but compatible restriction enzymes; and b) allowing ligation to take place, wherein ligation of said double-stranded DNA molecules in desired orientations generates molecules that are not cut by either of said restriction enzymes whereas ligation in undesired orientations generates molecules that retain at one or more ligation points a restriction site that is recognised by one of said restriction enzymes; and c) cutting the ligated DNA molecules with one or both of said restriction enzymes such that only molecules that are ligated in undesired orientations are cut, leaving a library of DNA molecules of varying length and sequence in a desired orientation.

* * * * *